(12) United States Patent  
Burdette

(10) Patent No.: US 11,890,493 B2  
(45) Date of Patent: Feb. 6, 2024

(54) NONINVASIVE TRANSVAGINAL ACOUSTIC THERMAL TREATMENT OF FEMALE STRESS URINARY INCONTINENCE

(71) Applicant: ACOUSTIC MEDSYSTEMS, INC., Savoy, IL (US)

(72) Inventor: Everette C. Burdette, Savoy, IL (US)

(73) Assignee: Acoustic Medsystems, Inc., Savoy, IL (US)

( * ) Notice: Subject to any disclaimer, the term of this patent is extended or adjusted under 35 U.S.C. 154(b) by 535 days.

(21) Appl. No.: 16/412,581

(22) Filed: May 15, 2019

(65) Prior Publication Data

US 2019/0336796 A1 Nov. 7, 2019

Related U.S. Application Data

(63) Continuation of application No. 14/410,984, filed as application No. PCT/US2013/047939 on Jun. 26, 2013, now Pat. No. 10,307,620.

(60) Provisional application No. 61/665,300, filed on Jun. 27, 2012.

(51) Int. Cl.

| A61N 7/02 | (2006.01) |
| A61B 8/12 | (2006.01) |
| A61B 8/08 | (2006.01) |
| A61B 17/00 | (2006.01) |
| A61B 18/00 | (2006.01) |
| A61N 7/00 | (2006.01) |

(52) U.S. Cl.
CPC .............. *A61N 7/02* (2013.01); *A61B 8/0841* (2013.01); *A61B 8/12* (2013.01); *A61N 7/022* (2013.01); *A61B 2017/00805* (2013.01); *A61B 2018/00523* (2013.01); *A61N 2007/0078* (2013.01); *A61N 2007/0082* (2013.01); *A61N 2007/025* (2013.01)

(58) Field of Classification Search
CPC .. A61N 7/02; A61N 7/022; A61N 2007/0082; A61N 2007/0078; A61N 2007/025; A61B 8/0841; A61B 8/12; A61B 2017/00805; A61B 2018/00523

See application file for complete search history.

(56) References Cited

U.S. PATENT DOCUMENTS

| 4,957,099 | A | | 9/1990 | Hassler |
| 5,443,069 | A | * | 8/1995 | Schaetzle ........... A61B 17/2258 601/3 |
| 5,471,988 | A | * | 12/1995 | Fujio ................... A61B 8/4272 601/3 |
| 7,211,044 | B2 | | 5/2007 | Mast et al. |
| 2002/0055679 | A1 | | 5/2002 | Sati et al. |
| 2003/0178032 | A1 | | 9/2003 | Ingle et al. |
| 2006/0074314 | A1 | | 4/2006 | Slayton et al. |

(Continued)

OTHER PUBLICATIONS

Diederich, C., "Thermal Therapy Mediated Effects", retrieved from the Internet: <URL: http://www.aapm.org/meetings/amos2/pdf/42-11935-44165-58.pdf>, fig. 1, 9, 16, 19, 20, 7 pages.

(Continued)

*Primary Examiner* — Hien N Nguyen
(74) *Attorney, Agent, or Firm* — Foley & Lardner LLP

(57) ABSTRACT

Systems and methods for transvaginal high intensity concentrated ultrasound. Urinary incontinence is treated through application of high intensity ultrasound to tissue structures to affect a change in the tissue.

14 Claims, 29 Drawing Sheets

(56) References Cited

U.S. PATENT DOCUMENTS

2006/0235300 A1 10/2006 Weng et al.
2008/0228075 A1 9/2008 Fraser et al.
2010/0049186 A1 2/2010 Ingle et al.
2013/0131668 A1 5/2013 Schaer

OTHER PUBLICATIONS

International Search Report for PCT/US2013/047939, dated Nov. 7, 2013, 2 pages.
Notification of Transmittal of the International Search Report and Written Opinion of the International Searching Authority, or the Declaration for PCT/US2013/047939, dated Nov. 7, 2013, 7 pages.
Office Action in U.S. Appl. No. 14/567,559, dated May 1, 2017, 11 pages.

* cited by examiner

Dynamic Axial and Directional Control of Heating
Experiment–*ex vivo* and *in vivo*

Angular Control
Sectored Tubular Radiators
Pre-Selected Directivity

Radial Depth of Coagulation (mm)
— in vivo
— in vitro

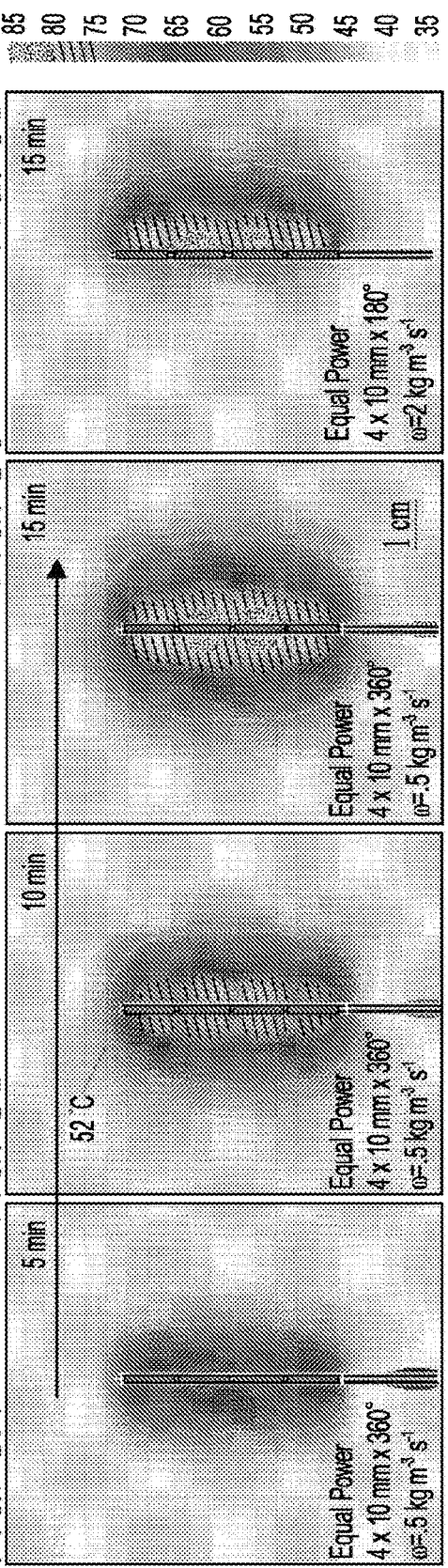
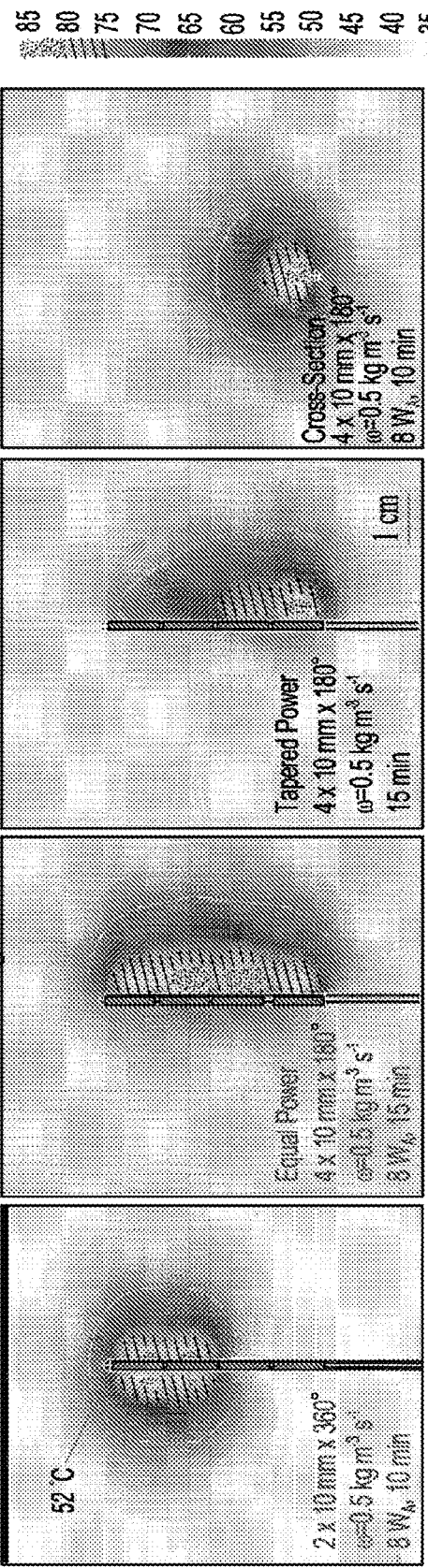

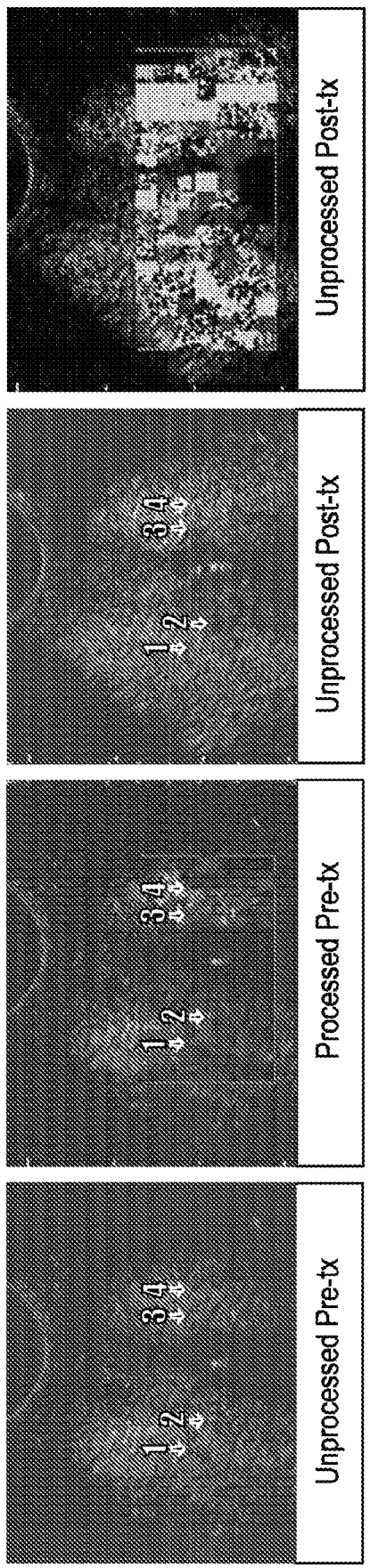
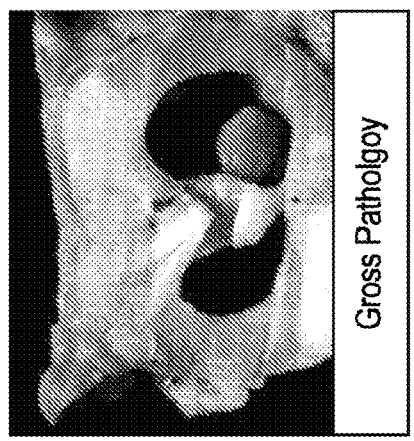
FIG. 8A Unprocessed Pre-tx
FIG. 8B Processed Pre-tx
FIG. 8C Unprocessed Post-tx
FIG. 8D Unprocessed Post-tx
FIG. 8E Gross Patholgoy 90° sector Tubular, 6.5 MHz,
$T_{control}$ = 60°C Planar, 6.5 MHz,
$T_{control}$ = 60°C Curvilinear, 6.5 MHz,
$T_{control}$ = 60°C Dual-Sector
Lateral 90 deg. Sonication Wide Angle Triple-Sector
Lateral 90 deg. &
Posterier 60 deg.
Sonication

NONINVASIVE TRANSVAGINAL ACOUSTIC THERMAL TREATMENT OF FEMALE STRESS URINARY INCONTINENCE

CROSS-REFERENCE TO RELATED APPLICATIONS

This application is a continuation of U.S. patent application Ser. No. 14/410,984 filed Dec. 23, 2014, which is a U.S. National Phase application of PCT/US2013/047939 filed Jun. 26, 2013, which claims priority to U.S. Provisional Application No. 61/665,300 filed Jun. 27, 2012, all of which are incorporated herein by reference in their entirety.

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

Urinary Incontinence is a significant, and growing, concern for women with a prevalence of 53.2%. The total cost of treating urinary incontinence in 1995 was $26.3 billion. Urinary incontinence (UI) affects more then 35 million Americans, most of whom are women. Approximately 12 million women sought physician treatment for UI in 2004. That number is expected to grow to 16.3 million in 2010.

Factors contributing to UI in women include anatomic (a shorter urethral length and a disruption of the urethral support as a result of vaginal delivery), genetic, obesity, diabetes, etc. All of these factors are increasing with the shift of population demographics. Stress Urinary Incontinence ("SUI") is the predominant form of UI and is primarily caused by a weakened pelvic floor which leads to hypermobility, or the movement of the urethra under exertion. SUI is the most common type of urinary incontinence in women. Risk factors for stress incontinence include female sex, advancing age, childbirth, smoking, and obesity. Conditions that cause chronic coughing, such as chronic bronchitis and asthma, may also increase the risk and/or severity of symptoms of stress incontinence.

SUI is a bladder storage problem in which the urodynamics of the urinary tract are altered (typically through childbirth), and the sphincter is not able to prevent urine flow when there is increased pressure from the abdomen. Stress incontinence may occur as a result of weakened pelvic muscles that support the bladder and urethra, or because of malfunction of the urethral sphincter. Both of these lead to a reduction in the pressure required to pass urine through the urethra. Thus, increases in pressure from everyday activities can cause the emission of a small amount of urine. Approximately 50% of women in the US have occasional urinary incontinence and approximately 14 million of them present with symptoms of SUI which require intervention. Most women accept the inconvenience of incontinence, utilizing pads and protective underwear as a silent treatment option.

The realignment of the urethra during acts such as lifting, laughing, coughing, or many daily activities can change the hydrodynamics of the bladder-urethral plumbing, resulting in unintended urinary leakage. Pharmaceuticals are the primary physician-directed treatment, representing $1.2 billion in annual expenditures. Pharmaceuticals and pads do not provide permanent relief, but impose a constant economic drain with undesirable physical side-effects. An additional factor of significance is the effect on depression in sufferers. It has been determined that after adjusting for morbidity, functional status, and demographic variables, women with severe and mild-moderate incontinence were 80% and 40%, respectively, more likely to have depression than continent women.

Hypermobility may be treated surgically by the insertion of a tape between the vaginal wall and the urethra to act as a sling for the urethra to diminish unintended urinary leakage. There were 175,000 sling procedures performed in the US in 2004. The use of bulking agents to decrease urethral diameter and compliance has also shown some success, with 60,000 bulking procedures performed in the US in 2004. In attempts to replace invasive surgery and implants with minimally invasive approaches, work has been performed by Dmochwski, Ross, and Fulmer to show some clinical utility to thermally remodeling the collagenous structure of the pelvic floor to reduce hypermobility.

In the 1990s the standard procedure was to apply a "sling" by wrapping a sheet of material around the urethra (inserted through a vaginal incision, placed between the urethra and vagina, and attach at both ends to the pubis). The "sling" or "hammock" formed thusly would replicate a healthy endopelvic fascia. That is, it would pull the urethra in a superior/posterior direction, restoring normal anatomy and increasing the hydrostatic pressure required to void the bladder. Additionally, and just as important, the sling is less prone to deformation under pressure than the damaged endopevic fascia. This treatment is still performed today and is prevalent in cases where the integrity of the endopelvic fascia is so degraded that the bladder prolapses into the vagina.

One of the primary treatments employed today is endoscopic placement of a narrow tape (1 cm wide by 40 cm long) through a single incision in the midline of the vagina, just below the urethra. The tape is pulled taught through two suprapubic incisions and held in place by tissue formation during the healing process. The tape material is less elastic than the damaged endopelvic fascia and more resistant to distension during periods of exertion.

There are published improvement rates of greater than 90% and cure rates greater than 80%. The interventions are surgical, however, and require significant anesthetic intervention as well as incisions in the vagina and (in the case of transvaginal tape) in the suprapubic region. Failure rates are reported in the 5% to 10% range and consist primarily of bladder perforation, immediate post-procedure retention, infection, and novo incontinence at some period post procedure.

A minimally invasive approach using radiofrequency (RF) electrical current to heat and remodel the endopelvic fascia has been attempted in recent years. Radiofrequency Bladder Neck Suspension (RFNS) requires exposing the endopelvic fascia via two 2 cm incisions through the mucosal and submucosal membranes of the superior/lateral aspects of the vagina. A bipolar radiofrequency probe is applied to the exposed endopelvic fascia, inducing resistive heating as the alternating current passes through the tissue. RF thermal remodeling of the endopelvic fascia causes the collagenous structure to remodel and shrink. The treatment does affect a positive benefit, with longer-term cure rates at greater than 75%. The underlying science of this approach is sound as thermal energy shrinks the collagen by affecting the basic structure of the molecule. Collagen is typically a triple helical chain of proteins, with cross-linking along the chain to maintain the structure. Wall and others have confirmed that thermal remodeling of collagen does occur in different time intervals in relation to elevated temperatures.

Minimally invasive attempts at radiofrequency (RF) remodeling of the endopelvic fascia have been inconsistent because the physics of RF ablation (including tissue resistivity variability) do not allow the consistent of predictable application of therapeutic levels of energy at levels as deep as 10 mm and without causing injury to the vagina.

SUMMARY OF THE INVENTION

One implementation of the invention relates to a system for treating stress urinary incontinence. The system includes an applicator having at least one transducer array and an acoustic coupling balloon.

Another implementation of the invention relates to a method of treating urinary incontinence. An anatomic structure to be treated is identified. The treatment focal depth and focal zone are mapped. Acoustic energy is applied to raise the temperature of at least a portion of the anatomic structure to 50° C. to 80° C. for a short time period sufficient to affect remodeling of the collagenous structure of the portion of the anatomic structure. Changes in tissue density and elasticity in and around the anatomic structure are noninvasively monitored.

Another implementation of the invention relates to a computer-implemented system for treatment of stress urinary incontinence. The system includes a processor and a tangible computer-readable medium. The computer readable medium is operatively connected to the processor and includes computer code configured to: identify an anatomic structure to be treated; map the treatment focal depth and focal zone; apply acoustic energy to raise the temperature of at least a portion of the anatomic structure to 50° C. to 80° C. for a short time period sufficient to affect remodeling of the collagenous structure of the portion of the anatomic structure; and noninvasively monitoring changes in tissue density and elasticity in and around the anatomic structure.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIG. 1A illustrates the use of a urethral acoustic wand for transurethral treatment for bladder neck stabilization and 1B illustrates the use of a urethral acoustic wand for treatment of the endopelvic fascia, musculature, and connective tissues for pelvic floor stabilization and FIGS. 1C-D illustrate a transvaginal high intensity concentrated ultrasound wand that transmits energy through the vaginal wall to affect thermal remodeling of collagen in the endopelvic fascia. Directional energy concentration leaves vaginal mucosal and submucosal tissue as well as urethral and periurethral tissue relatively unaffected. Heated collagen in connective tissues and endopelvic fascia shrinks to restore normal urethral anatomy in much the same manner as the "hammock" maintains proper urethral position. Additionally, new collagen formation is stimulated as a healing response to the heat treatment.

FIGS. 3A-H demonstrate angular and axial control of power deposition ($P^2$) and heating and zones of thermal coagulation. Applicators can be driven with power excitation to tailor temperature distribution in response to anatomy, dynamic changes in perfusion, etc. Applicator parameters for treating SUI (i.e., number/length of transducers, sectoring, curvature, focusing) are designed specifically for pelvic fascia targeting.

FIGS. 8A-E illustrate results from prostate studies comparing ultrasound image information from a mid-gland slice showing unprocessed pre (8A) and post (8C) heating and processed pre (8B) and post (8D) heating images of thermal dose and 4-week post-treatment prostate gross pathology (8E).

FIGS. 21C and 21D illustrate the thermal dosage cloud at 52 degrees C. for 3 minutes and 5 minutes respectively.

DESCRIPTION OF THE INVENTION

Figure 1A:
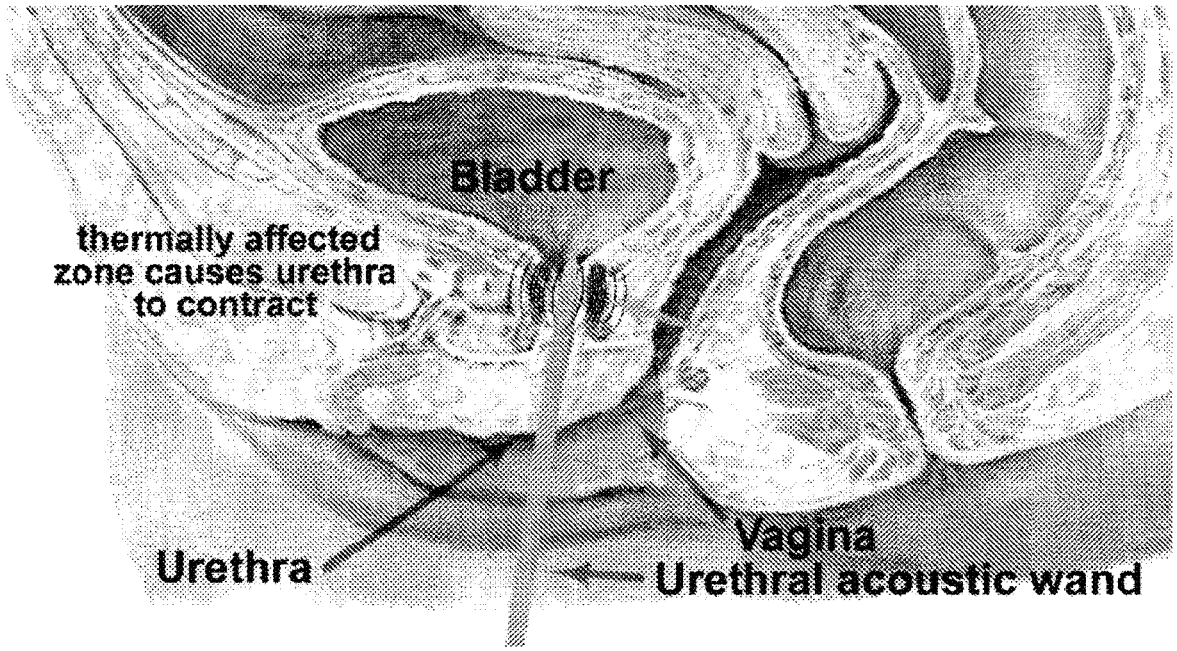
FIGS. 1A-D illustrate noninvasive treatment of Stress Urinary Incontinence (SUI): (1A) bladder neck stabilization, and (1B-D) Pelvic Floor Stablization.
Figure 1B:
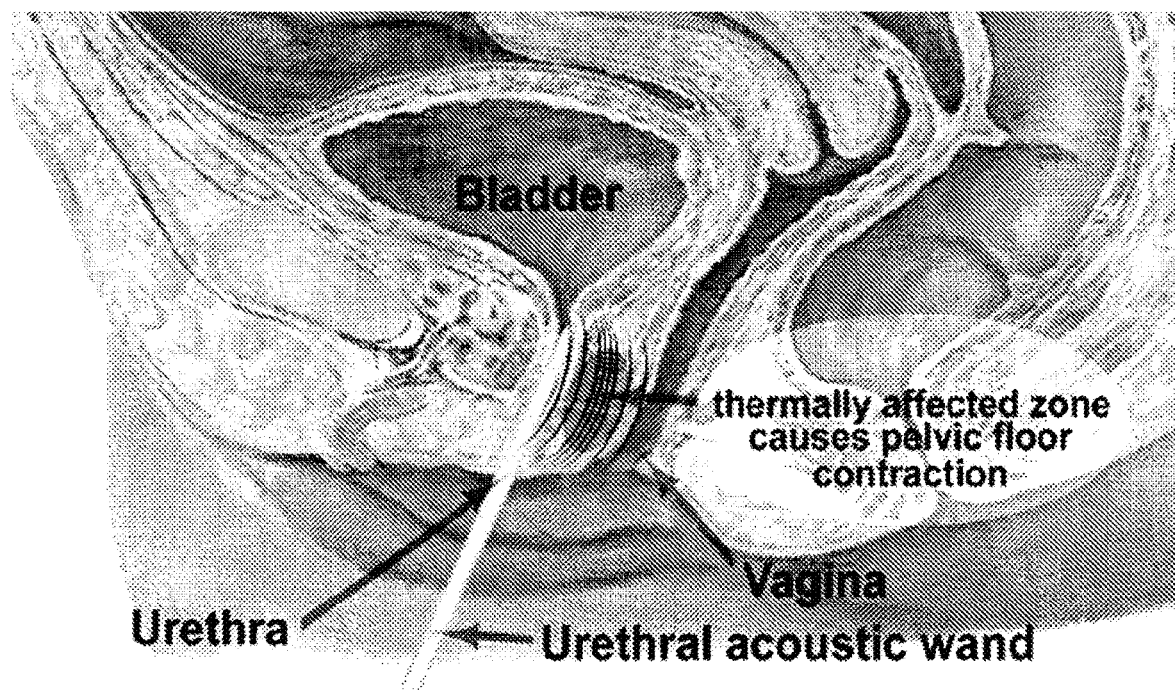
Figure 1C:
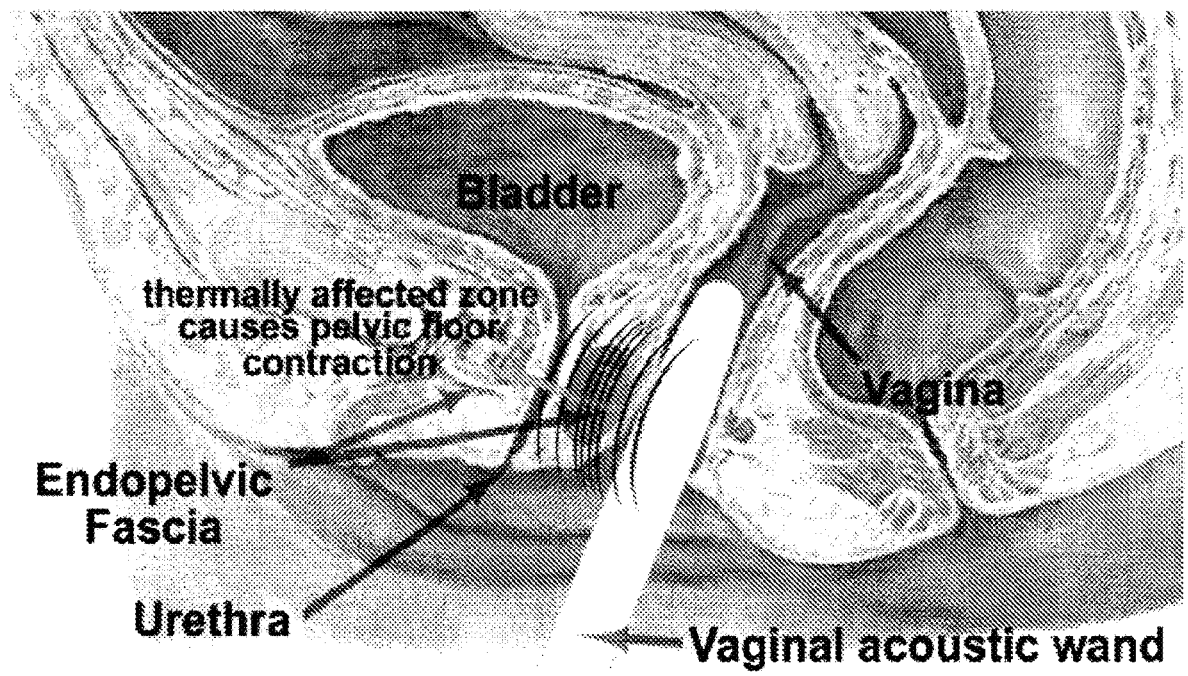
Figure 1D:
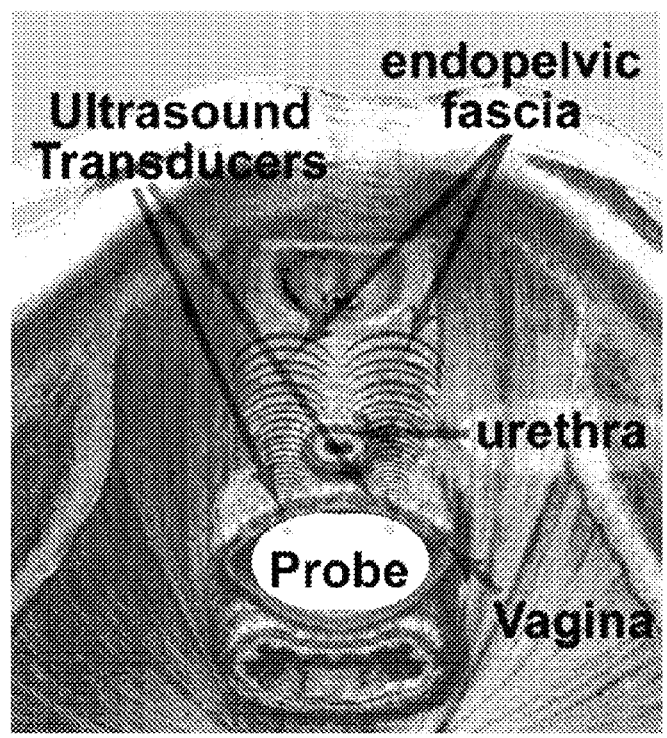
Figure 2A:
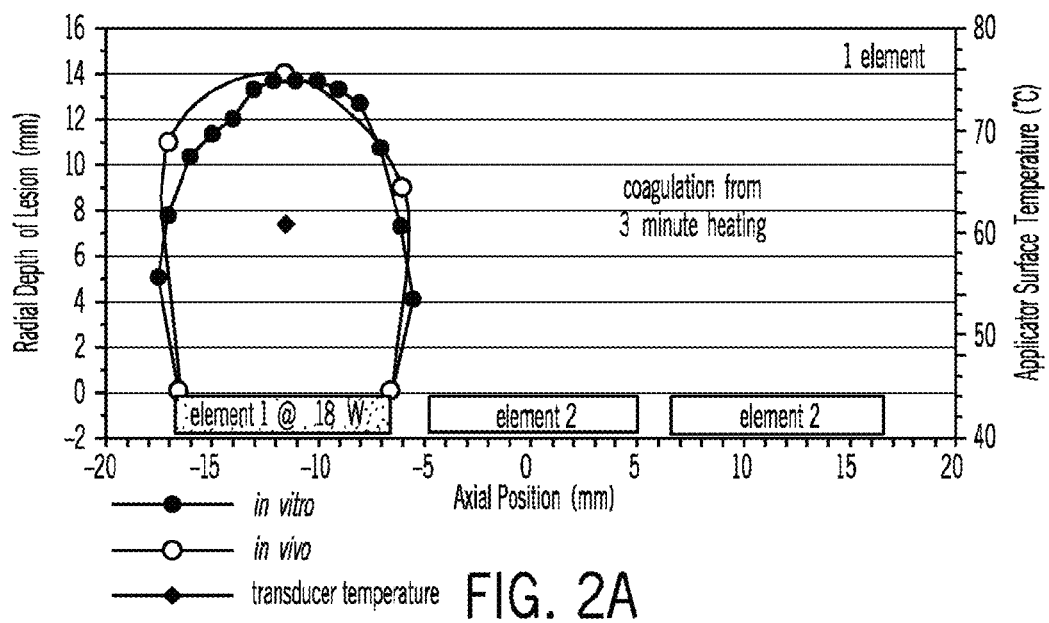
FIGS. 2A-F demonstrate angular and axial control of power deposition ($P^2$) and heating from in vivo measurements of temperature and zones of thermal coagulation. Applicators can tailor temperature distribution in response to anatomy, dynamic changes in perfusion, etc. Applicator parameters (i.e., number/length of transducers, curvature, and focusing as needed) is designed specifically for pelvic fascia targeting.
Figure 2B:
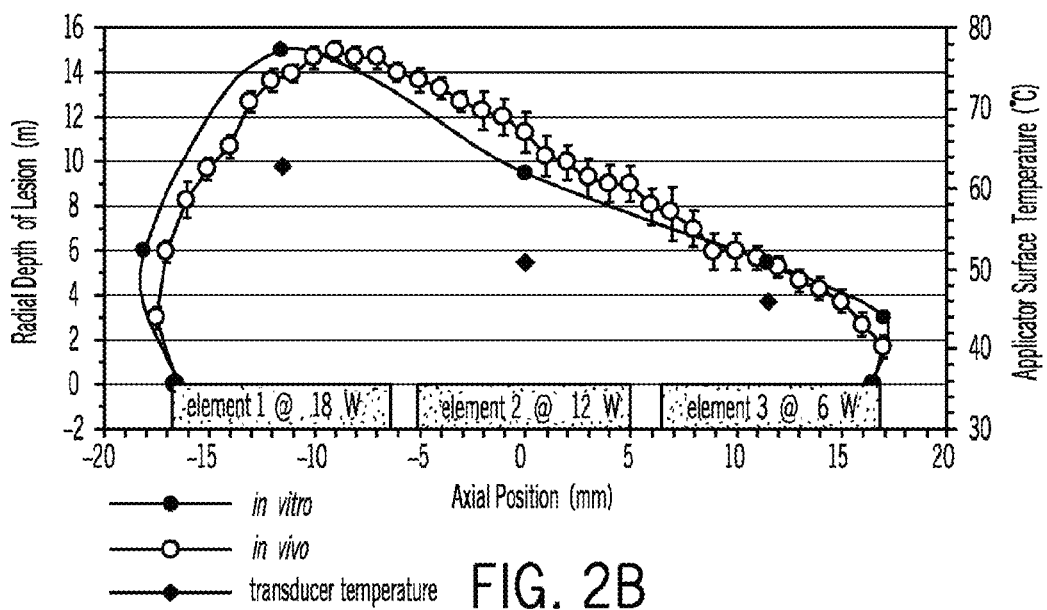
Figure 2C:
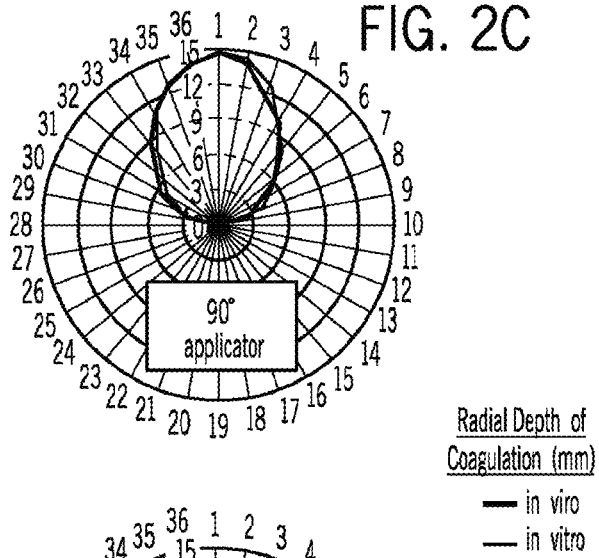
Figure 2E:
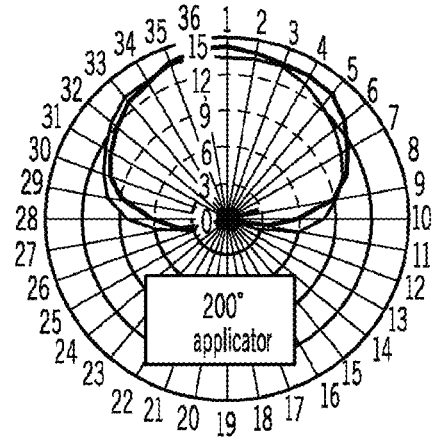
Figure 2D:
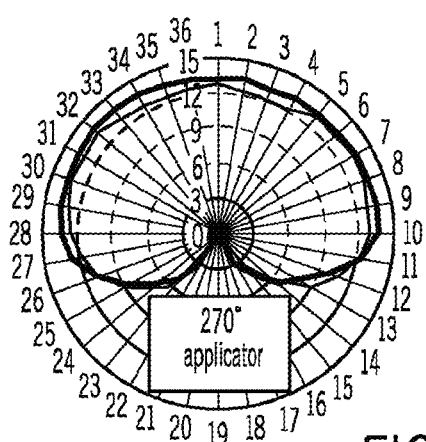
Figure 2F:
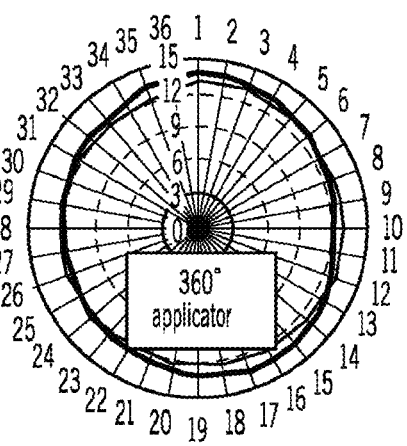

The invention is described in the following pages. All cited references are incorporated herein by reference in their entirety. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

Thermal modification (shrinkage and subsequent neocollagenesis) of the collagenated tissue structure of the endopelvic fascia in females has been shown to be helpful in the treatment of stress urinary incontinence (SUI), either as a sole modality or as an adjunct to surgical treatment or other treatments such as injectables. Further, if that treatment may be performed without incisions and with optimized thermal energy deposition control, such treatment may be performed in an outpatient (or office-based) setting, with no anesthesia or minimal sedation, and at significantly lower cost than existing treatments. The approach of the present invention provides a noninvasive and inexpensive treatment with a minimal level of associated discomfort for the treatment of SUI which could be performed on an outpatient basis with only minimal sedation or local anesthesia. This treatment alternative would be potentially permanent as opposed to absorptive pads or undergarments, and would be less expensive than either the palliative absorptive pad or undergarment approach or injectables or the surgical intervention approach.

In one implementation, system and methods are provided to deliver treatment for thermal modification of the endopelvic fascia in a straightforward, non-invasive manner with Transvaginal High Intensity Concentrated Ultrasound (THICU) through a transvaginal approach. THICU should achieve the same positive results—or superior results—as RF remodeling of the endopelvic fascia. There currently exists clinical evidence that heating the ani levator region of the pelvic floor or tissue surrounding the bladder neck to produce shrinkage to stabilize the urethral pressure has a significant and positive clinical effect. Laboratory testing for this application have been performed which indicate that this unique soft-focused ultrasound technology can create lesions of the appropriate dimension to affect that change, which is corroborated by our related work in prostate.

In one implementation, a clinical therapy system is provided for Transvaginal Thermal Remodeling of the Endopelvic Fascia (TTREF) using a unique transvaginal probe which images, targets, and treats the tissue in the proper region to produce a lifting effect to the urethra. The mechanical impact on the urethra is believed to be similar to that of a surgically placed "hammock" or "sling" using a non-invasive device.

In one implementation, THICU applicators were integrated with ultrasound imaging transducers to provide both capabilities in a single device and incorporate software to target the proper tissues in the pelvic floor. The primary target is the ani levator region along the central 70% of the female urethra. These is able to provide acoustic energy, and dynamically adjust the pattern of energy delivery, to a localized zone (therapeutic zone) that is 0.5 cm to 2.0 cm deep beyond the applicator outer surface by incorporating multiple shaped transducer elements located in two regions on the vaginal probe designed as described below. The applicator will raise the temperature in the therapeutic zone to 50° C. to 80° C. while not exceeding 45° C. in adjacent tissue structures or vaginal wall.

The ultrasound transducer design dynamically concentrates acoustic energy in a near-planar therapeutic zone which is 3-15 mm thick (focal zone) at various depths (focal depths) within tissue structures to affect thermal remodeling of a collagenous structure. The prototype of an entirely noninvasive, real-time and low-cost technique for simultaneous monitoring and localized thermal treatment demonstrates excellent control. The thermally treated collagen-containing pelvic fascia has sufficiently distinct mechanical properties from the non-heated tissue so that elasticity difference between treated and untreated or pre-treatment tissue as well as tissue structural changes due to the thermal delivery can be imaged to localize, treat and monitor the treatment of the target region using noninvasive, thermal therapy techniques.

This method is used for simultaneous monitoring and ablation by combining the noninvasive aspect of highly controlled intense ultrasound therapy, the real-time capability of diagnostic ultrasound and the sensitivity of structural and elasticity imaging. These data are processed in real time using pattern recognition algorithms applied to the elasticity images.

In one implementation, a THICU probe is used to concentrate acoustic energy at distance of 0.5-1.5 cm from the applicator without overheating tissue adjacent to the probe or at depths beyond the target tissue and which incorporates an ultrasound imaging array for targeting and guidance.

One implementation of a system for real-time treatment and monitoring which includes software control algorithms for the THICU device and also incorporates the novel ultrasound generator and controller hardware and software described herein, and initial imaging analysis software based on the application of pattern recognition algorithms for imaging of acoustic modulated vibration displacement to determine its feasibility for treatment monitoring.

The THICU is shown capable of providing the new noninvasive tools for monitoring and generating remodeling of endopelvic fascia, and constitutes a novel, stand-alone, noninvasive, real-time and low-cost monitoring and image-guided intervention (IGI) tool for increasing the effectiveness and durability of treatment for SUI.

Probe design is not limited to the preferred embodiment illustrated and can accommodate the key design elements in many different embodiments to achieve optimal treatment delivery to the selected target tissue(s) and includes the system-level integration and control/monitoring algorithms. Included are the design, component performance, thermal treatment parameters and control, real-time therapy monitoring, and dose delivery.

The primary advantage of ultrasound is that THICU may affect thermal remodeling of the collagenous structure of the endopelvic fascia (noninvasively) by focusing acoustic energy through the vaginal wall or urethra and concentrating it on the endopelvic fascia (FIG. 1A-D). In addition, current thermal treatments are more invasive than tape or mesh procedures (two incisions vs one).

Aside from the obvious elimination of the need for incisions, there are other challenges associated with radiofrequency heating of tissue to achieve thermal remodeling of the endopelvic fascia that the THICU approach can potentially overcome. These challenges are associated with the inability of radiofrequency current to create homogeneous heating within tissue structures, a challenge which concentrated acoustic energy will address. Additionally, radiofrequency bladder neck suspension requires dissection of the vagina and urethra to expose the endopelvic fascia. The deformation of anatomy during treatment does not lend itself to remodeling the tissue in a manner which restores normal anatomic structure. THICU may be performed with a vaginally or urethrally inserted probe, without damaging the tissue structures of the urethra or vagina. This is further described below with regard to Preliminary Studies.

The THICU approach will require vaginal or urethral insertion of a probe with an ultrasound transducer. Acoustic energy is concentrated on the connective tissues, musculature, or endopelvic fascia at the lateral aspects of the urethra without the need for an incision. The resultant thermal remodeling of the collagenous structures in the endopelvic fascia will restore the structure to a more normal anatomy.

Certain treatment requires concentration of acoustic energy on a thin tissue structure which is some distance away from the vaginal wall. The resultant thermal dose is intended to remodel the collagenous tissue of the endopelvic fascia, inducing a shrinking of the tissue to restore normal anatomic structure without incurring damage to the vaginal wall or distant tissue. The technical challenge lies in (1) identifying the structure to be treated, (2) concentrating, or focusing, the acoustic energy on a thin structure while minimizing the temperature elevation on the vaginal tissue which is adjacent to the probe, or the urethral and periurethral tissue which is distant of the treated tissue to the endopelvic fascia, and (3) noninvasively monitoring the shrinkage of the collagenous structure of the endopelvic fascia and use those measurements as a control feedback for the therapy. Presently used technologies (laser, microwave, RF, etc.) have limitations due to fundamental physics and tissue interactions:

Thermal ablation not predictable or controllable (dynamic and heterogeneous tissue properties; direct interactivity with treatment energy source changes patterns)

Difficulty in targeting the treatment site

Target tissue is not properly treated (often inadequate)

Surrounding healthy tissue is often damaged

Limited treatment volume; potentially long treatment times

All current surgical interventions for treating SUI involve incisions or needle insertions through the urethral wall or vaginal wall, in some instances depositing or placing implants. Certain implementations described herein will (1) identify the anatomic structure (endoplevic fascia) to be treated; (2) map the treatment focal depth and focal zone; (3) apply acoustic energy to raise the temperature of the endopelvic fascia to 50° C. to 80° C. for a short time period to affect remodeling of the collagenous structure of the endopelvic fascia; (4) noninvasively monitor changes in tissue density and elasticity.

In one implementation, for multi-sectored design, two dead zones between sectors (60°) should be formed, with one anterior avoiding damage to prominent neural bundles between 5 and 7 o'clock between the urethra and vagina as viewed from urethra, and another dead zone aimed posterior to avoid damage to the rectum. Thus, 90-120° active sectors can be aimed anteriolateral.

In one implementation, frequency should be selected to potentially achieve start of heating zone >1 cm from device.

Given relatively small sectors and small transducer size, penetration of multi-sectored and curvilinear devices will likely be similar (Wootton et al, 2007 in *IJH*)

Treatment region most impacting for treating endopelvic fascia for SUI is mid-50% of urethral length with insonation directed transurethrally toward vagina with penetration of 5-15 mm Transvaginal Thermal Remodeling of the Endopelvic Fascia should produce the same, or superior, clinical benefits as Radiofrequency Bladder Neck Suspension, but without the associated morbidity. TTREF should, in fact, should produce benefits which will approach those of the "gold standard" treatment, surgically applied transvaginal slings, but without any incisions and the associated risks of bladder perforation, infection, etc. Because TTREF may be performed in an outpatient setting with local analgesics, the cost of the procedure should be much less than traditional surgical intervention, as well. Therefore, TTREF has the potential to replace many of the 235,000 surgical interventions now employed to treat stress urinary incontinence.

Preliminary Studies

Significant work in high intensity intracavitary and interstitial ultrasound that will facilitate the proposed research has been performed. Transducer design and control hardware and methods for simultaneous noninvasive monitoring using either acoustic amplitude modulated vibration/motion or cavitation (sub-harmonic, broadband), and pattern recognition learning-based ultrasound image analysis have been implemented. The inventor has developed high intensity intracavitary and interstitial ultrasound transducer arrays for the therapeutic treatment of prostate disease, as well as liver and kidney cancer.

1. Catheter-Based Ultrasound Technology for Thermal Therapy

Ultrasound-based interstitial/intracavitary applicators produce more controllable heating of clinical target volumes than other heating technologies, and have been extensively evaluated for interstitial hyperthermia for combination with radiation or drug therapy, as well as localized thermal ablation. The interstitial ultrasound applicators utilize arrays of small tubular ultrasound radiators, designed to be inserted within plastic implant catheters typically used for interstitial HDR brachytherapy. Water-flow is used during power application to couple the ultrasound and improve thermal penetration. Multi-transducer intracavitary and interstitial devices have been evaluated with transducer diameters between 1.2 mm-3.5 mm and outer catheter diameters between 2 mm (15 gauge) and 4.0 mm (12 Fr), respectively, with 1.5 mm OD transducers and 13 g (2.4 mm OD) catheters being the most common configuration. These applicators are fabricated with multiple tubular segments, with separate power control, so that the power deposition or heating pattern can be adjusted in real time along the applicator axis. The ultrasound energy emanating from each transducer section is highly collimated within the borders of each segment so that the axial length of the therapeutic temperature zone remains well defined by the number of active elements over a large range of treatment duration and applied power levels (FIGS. 2A-F).

Furthermore, the angular or rotational heating pattern can be modified by sectoring the transducer surface. In this fashion, active zones can be selected (i.e., 90°, 180°, or 360°) to produce angularly selective heating patterns (FIGS. 2A-F). The orientation of these directional applicators within a catheter can be used to protect critical normal tissue or dynamically rotated and power adjusted to more carefully tailor the regions of heating. We have also fabricated applicators with sectioned cylindrical transducers having a radius of curvature greater than that of the catheter which results in a focal zone outside the catheter at a designed depth within the target tissue. Multi-applicator implants of interstitial ultrasound applicators have been demonstrated to produce contiguous zones of therapeutic temperatures and dose between applicators with separation distances of 2-3 cm, while maintaining protection in non-targeted areas. For the interstitial ultrasound devices with tubular sources, the radial penetration of energy falls off as $1/r$ with exponential attenuation and compares favorably to the $1/r^2$ losses of RF needles and $1/r^n$ (n=1-3) losses of microwave antenna. The spatial control along the length of these ultrasound applicators is superior to all other interstitial devices, with axial control defined by active elements over a large range of applied power and durations. Operating at high power levels, single applicators can generate substantial size thermal lesions ex vivo and in vivo (porcine thigh muscle and liver, canine brain and prostate) up to 21-25 mm radial distance, within 5-10 min treatment times, while maintaining axial and angular control of lesion shape (FIGS. 2A-F and FIGS. 3A-F). These ultrasound applicators provide the highest level of controllability, and provide more uniform and penetrating heating than all other interstitial heating techniques. The performance, feasibility, and safety of these devices and driving hardware have been demonstrated in numerous in vivo evaluations within canine, porcine, and ovine animal models. These devices and driving hardware can be compatible with MRI and MR thermal imaging.

Figure 4A:
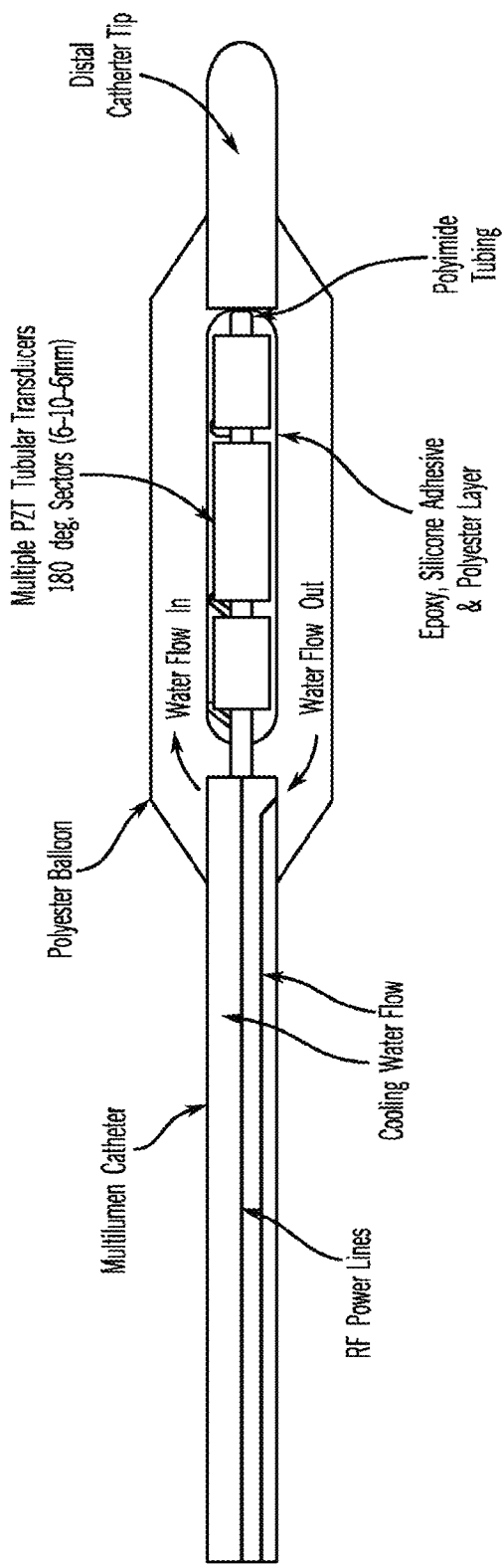
FIGS. 4A-B illustrate a transurethral ultrasound applicator, with integrated cooling and flexible catheter, sectored for 180°-angular selective thermal therapy.
Figure 4B:
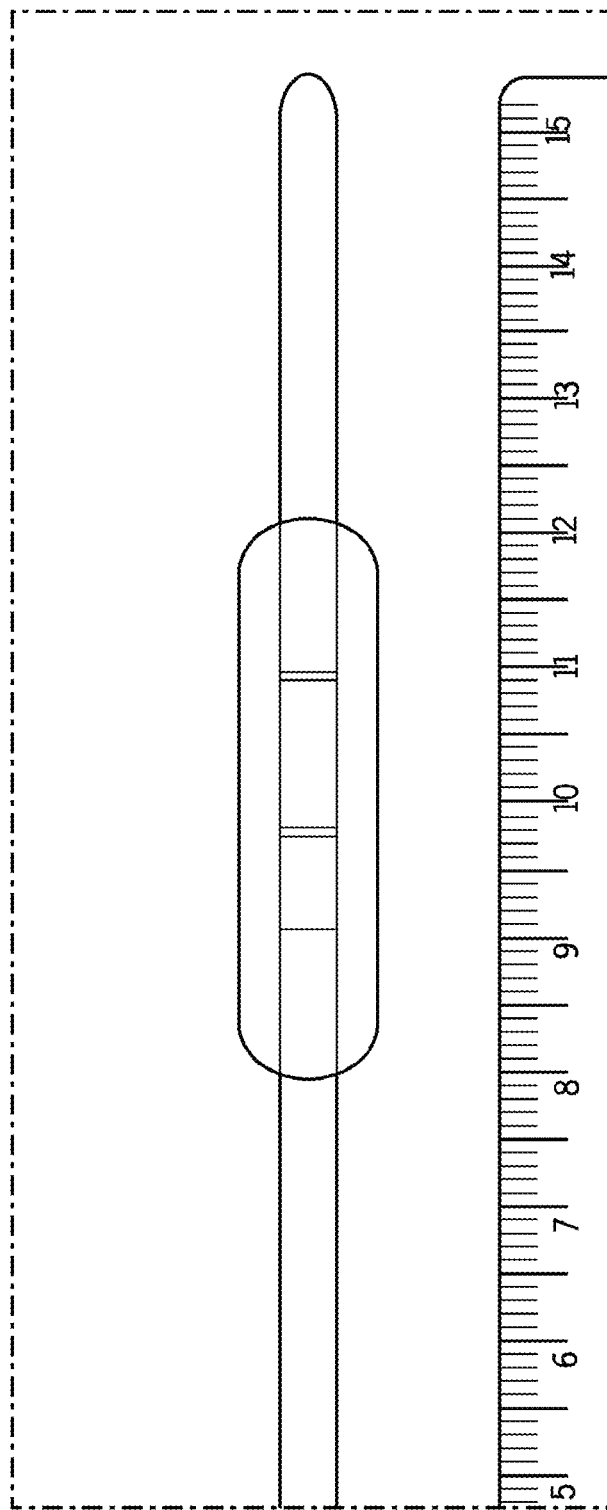
Figure 5:
FIG. 5 illustrates MR thermal imaging can be used to map the temperature elevations and thermal dose boundary (outer contour line) during the application of power/treatment, as demonstrated for high-temperature application for in vivo prostate treatment (3 slices, 6 mm apart). This result demonstrates thermal ablative temperatures in perfused tissue from cooled 3.5 mm OD transducer array. A similar design will be extended to treatment of SUI, but with less focal depth.

Catheter-based applicators with larger diameter transducers and thin walled catheters or integrated balloons have been designed and evaluated for transurethral prostate thermal ablation therapy using theoretical and in vivo animal studies (FIG. 4). These devices utilize multiple tubular transducer segments (2.5-3.5 mm OD, 6-10 mm long, 3-4 elements), each with separate power control, so that the power deposition or heating pattern could be adjusted in real time in the axial dimension. In addition, the tubular transducer segments were modified to produce angularly directional heating patterns such as 180° or 270° acoustic emission. Invasive temperature measurements in vivo demonstrated that these directional applicators could direct the energy and destroy defined target regions such as the anterior—lateral regions of the prostate gland while avoiding non-targeted areas (e.g., rectum). These directional (180°) transurethral ultrasound applicator have been evaluated in canine prostates in vivo using multi-slice MR temperature imaging (MRTI) on a 1.5 Tesla magnetic resonance imaging (MRI) unit, clearly demonstrating spatial control of ablative heating (180° heating patterns of variable length, 15-20 mm radial penetration extending to the prostate boundary, and less than 15 min treatment duration) and the ability to monitor therapy using MRTI (FIG. 5). These efforts demonstrate that we can develop ultrasound devices with integrated cooling, power output levels required for tissue ablation, and angular and axial spatial control to successfully target specific tissue regions while avoiding adjacent sensitive tissues if necessary.

Figure 6:
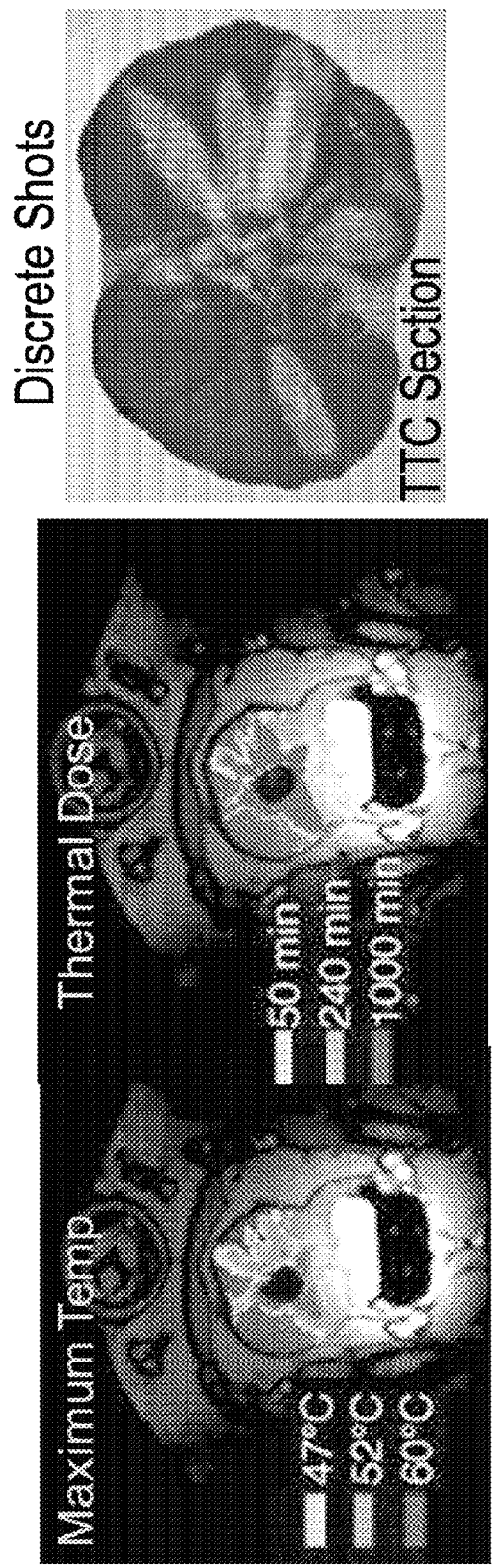
FIG. 6 illustrates MRTI guided thermal coagulation demonstrating discrete shots with a focused curvilinear applicator in prostate. Thermal dose, temperature and TTC stained tissue section are shown. A tissue section is shown for a case of multiple discrete shots with a curvilinear applicator demonstrating distinct lesions, separation and protection of the urethra, coagulative temperatures with sharp margins between treated and normal viable tissues, and extending out to 15 mm radius in this particular configuration. For our application in treating incontinence, higher frequencies, tighter radius of curvature, and wider elements could be used to more tightly define our region of coagulation in both width and depth.
Figure 7:
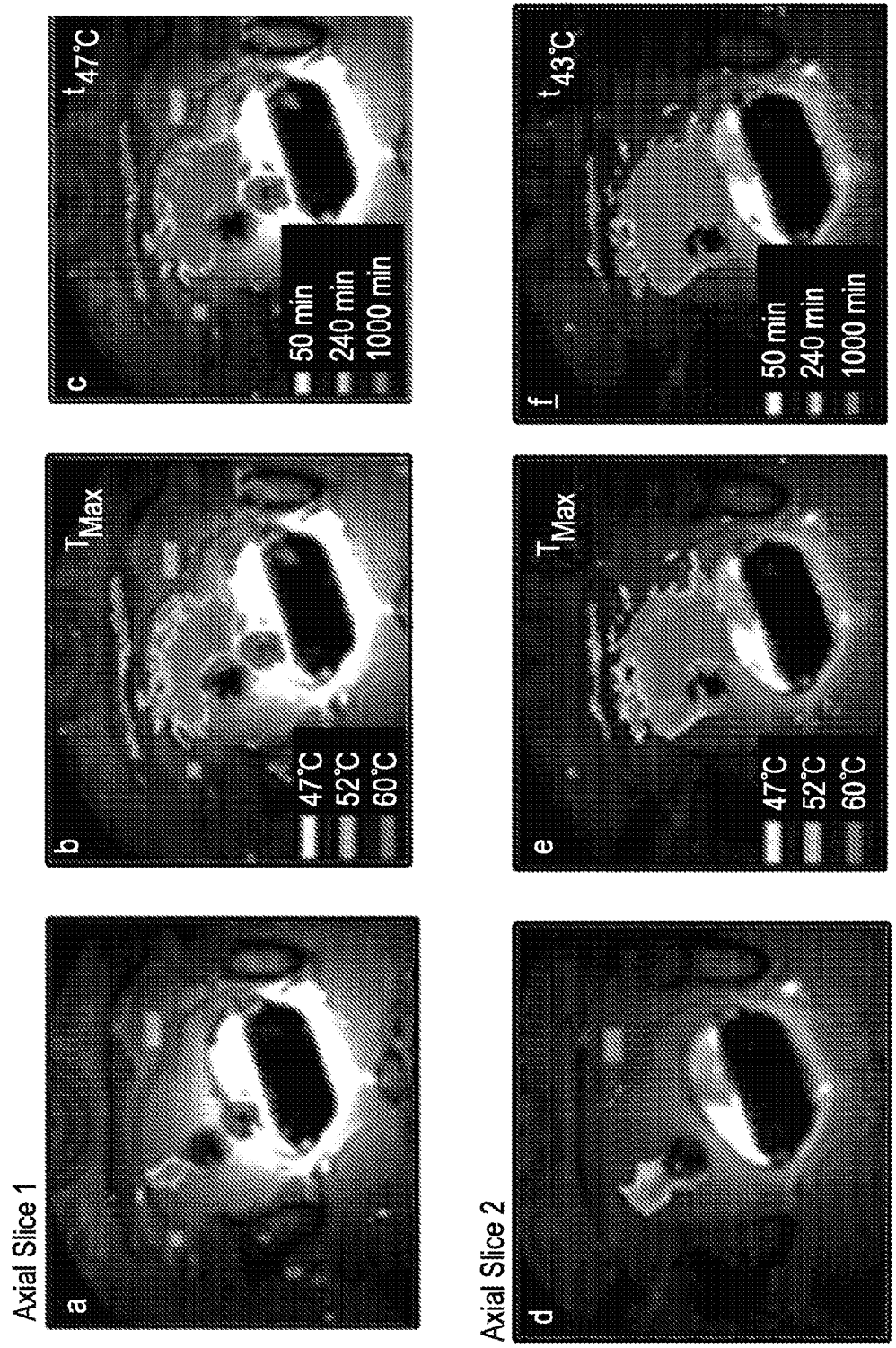
FIG. 7 illustrates MRT temperature and thermal dose for treatment of a 180° prostate section using a focused curvilinear transurethral applicator with discrete rotation. The temperature was controlled to 52° C. to the outer boundary of the prostate. Real-time temperature (a,d) during a treatment, cumulative temperature (b,e), and thermal dose maps (c,f) are shown for imaged tissue slices, centered on each transducer section.

2. Catheter-Based Ultrasound Applicators with Highly-Selective Ablative Heating Patterns Three different configurations of directional transurethral and transvaginal applicators, designed for rotational positioning and sweeping, have been evaluated in vivo: (1) 90° sectored tubular, (2) planar, and (3) lightly focused curvilinear devices. Each applicator configuration consisted of two transducer sections (3.5 mm×10 mm long, 6.5-8 MHz), mounted on a 4 mm delivery catheter with an inflatable 10 mm cooling balloon. The intracavitary cooling balloon lowers the thermal exposure of the mucosal tissue and vaginal lining (1-3 mm) below necrotic levels. The transducer assembly can be rotated in discrete steps to sweep the heating zone and conform to a larger volume. For prostate treatments, a water-cooling jacket on the endorectal coil provides cooling of the rectum and similarly, in some implementation present invention, an acoustically transparent thin balloon covers the transducers within the transvaginal probe to cool the vaginal wall. The 90° sectored tubular produces ~80-90° coagulation zone extending to prostate capsule within 10 min, and can be swept in 45° steps to treat the whole gland within ~30 min. The planar applicator produces narrow (~30°) coagulation zones with faster penetration, which can be rotated in 10-15° steps to treat larger volumes. The curvilinear transurethral applicator produces the most selective heating (~20 sector, 15-20 mm penetration), and can produce well-defined discrete shots (FIG. 6.) or be finely controlled with MRTI to tightly conform the thermal ablation to the outer prostate boundary (FIG. 7). The extent of the 52° C. contour was useful for determining extent of damage and rotation interval.

Following similar design principles, multi-sectored tubular transurethral applicators (three separately controllable 120° sectors on each transducer) were devised to allow for electronic control of the angular heating pattern without the need for rotation. In vivo evaluation demonstrated there is no apparent dead-zone or scalloping pattern in the coagulation zone, and that fast coagulation with angular control can be achieved. Longitudinal (sagittal) or axial imaging planes can be used to tightly control the heating distribution to the targeted boundary with these devices. For the SUI application, multiple sectors and various illumination schemes can be applied to treat larger target regions of the fascia or a smaller target region with excellent spatial control and less manipulation than any other method.

3. Theory

An acoustic and biothermal model of internally-cooled interstitial ultrasound applicators has been adapted and improved upon to include 180° catheter-cooled interstitial devices, intracavitary cooling, and the 90° tubular, planar, and curvilinear transurethral applicators within prostate. Dynamic sweeping or rotation of the applicator during the treatment is also incorporated. This transient finite-difference model is based upon the Pennes Bioheat equation. In order to improve accuracy, this model incorporates dynamic tissue changes in response to accumulation of thermal dose. Specifically, at $t_{43}=300$ min the blood perfusion reduces to zero and at $t_{43}=600$ min the acoustic attenuation increases 1.5-2 times. This dynamic approach has been used for transurethral and interstitial ultrasound applicators and shown to be in excellent agreement with experiment. The thermal dose distribution is calculated using the Sapareto-Dewey formulation and $t_{43} \geq 240$ min is used to define the boundary of thermal necrosis, as first proposed by Damianou et al., validated experimentally, and is currently used in clinical MRI guided thermal therapy systems. The model accepts variable convective heat transfer coefficients, heat capacity, thermal conductivity, density, perfusion, and acoustic attenuation within applicator structures and surrounding tissue.

The power deposition is determined by numerical solution of the Rayleigh-Sommerfield diffraction integral using the rectangular radiator method. The components of this model have been proven accurate and provide a tool for studying applicator design and developing treatment strategies for various treatment site applications. This model has been used to evaluate and compare the different types of catheter/obturator based directional ultrasound applicators. This thermal simulation software package was used to model the thermal treatment of incontinence and develop designs for transurethral and transvaginal applications.

4. Noninvasive Monitoring of Therapy

We have utilized abstract pattern recognition techniques in combination with expert system technology applied to ultrasound backscatter image measurements for real-time monitoring of thermal distribution within the prostate during thermotherapy. This approach allows real-time measurement of thermally-induced tissue necrosis. The basis of the method includes capturing baseline image data immediately prior to thermal therapy to determine initial parameters and using pattern recognition algorithms developed in our laboratory to monitor and analyze changes as thermal therapy procedure progresses which correlate with thermally-induced tissue changes.

Ultrasound backscatter image data over a 2D spatial plane covering region of interest were processed pre, during, and post thermal therapy to develop determinants for extraction of patterns that correlate with tissue changes (elasticity, density) during heating. The system was initially tested using a canine model, where prostates were heated and temperature and thermal dose maps were made from measured interstitial temperature sensors located within the prostate. Simultaneously with heating and collection of thermal data, ultrasound image data were processed in real-time using the expert system.

Correlation of the measured temperature data within the image field and the extracted patterns from the pixel analysis within the images yielded pattern determinants that accurately "tracked" with temperature (r=0.9, p=0.05 over 14 cases) and thermal dose (r=0.87, p=0.05 over 14 cases). These pattern determinants were represented as a color-coded 2D spatial map of prostatic heating, which was displayed as an overlay on the ultrasound image in real time. Results demonstrated that changes in thermal dose during the course of thermotherapy could be monitored non-invasively.

5. Significance of Preliminary Data

The directional catheter-based directional devices are selective in their ability to target predetermined regions of target tissue, and can be rotated in discrete steps or patterns electronically controlled to conform treatment to prescribed boundaries. The curvilinear applicator is the most precise of these directional techniques, followed by planar and convex shaped devices. Multi-sectored transurethral applicators, with dynamic angular control of heating and no rotation requirements, offer a fast and less complex means of treatment with selective contouring. The effective heating penetration for each design for SUI is between 0.3-1.5 cm extending from the cavitary wall to the outer target zone boundary as determined by imaging or range-gated pulsed acoustic signal analysis. For the latter, the therapy transducer can be used. For initial confirmation of the new acoustic methods, MR thermal imaging and dose maps, obtained in multiple slices through the target volume, have been useful for controlling therapy delivery (rotation, power levels) and assessing treatment. The experience gained from this work is directly applied to transurethral and transvaginal treatment of the zone of endopelvic fascia affecting urinary incontinence.

It is demonstrated that catheter-based ultrasound applicators are capable of controlled and penetrating heating of targeted tissue for hyperthermia and thermal ablative therapy, with significant improvement over existing heating technologies such as RF, laser, and microwave. These devices have been designed and fabricated within our labs, indicating that we have designed, built, tested, and implemented the technology used for the targeted thermal therapy for treating SUI. The general design of these catheter-based ultrasound devices allow for a high-degree of spatial control over the power deposition and resultant heating pattern, such that: dynamic control of the applied power levels along multielement applicators can be used to tailor and isolate heating along the length of an applicator; angular directivity of heating is possible to either protect or preferentially heat a target; favorable energy penetration makes a larger volume heating more practical. Biothermal simulations have demonstrated the capability to use these interstitial or catheter-based heating devices to produce effective heating patterns for treating a variety of tissues, with different acoustic and thermal properties, as well as different perfusion rates. This modeling package can be used for evaluation of various applicator designs and development of treatment strategies to accurately control the treated volume. Finally, this catheter-based ultrasound technology has been evaluated for compatibility with MRI thermal imaging via in vivo heating studies in phantoms, canine prostate and brain.

The directional transurethral and transcavitary (i.e. transrectal) devices are selective in their ability to target regions of the prostate gland, and can be rotated in discrete steps to conform treatment to prescribed boundaries. An analogous approach is used for heating the connective tissue and endopelvic fascia for treating SUI. The curvilinear applicator is the most precise of these directional techniques. Multi-sectored applicators, with dynamic angular control of heating and no rotation requirements, offer a fast and less complex means of treatment with less selective contouring. The effective heating penetration for each design (depending upon operating frequency and curvature) is between 0.3-2.0 cm extending from the urethra to the outer prostate capsule. For our SUI application the curvature and frequency is optimized to heat a region from 0.3-1.5 cm from the applicator. We have developed and tested ultrasound imaging based methods for monitoring to direct, and assess the effectiveness of thermal fascial reformation therapy of the pelvic fascia.

Guidance by ultrasound imaging is used to target the treatment region transvaginally (or transurethrally) to the endopelvic fascia and levator ani. Amplitude modulated acoustic vibration imaging coupled with our image pattern recognition algorithms provide noninvasive monitoring of treatment in conjunction with image guidance.

EXAMPLES

A prototype system consisting of therapy applicators, a generator-controller system, and a monitoring system is described. The acoustic applicators consist of transducer arrays arranged at two different positions within a transvaginal applicator. The transducers are driven by a computer-controlled multi-channel RF generator. The power and frequency to each transducer is software controlled. The applicator designs are based upon simulations and parametric studies of interactive parameters, followed by fabrication and bench testing. Radiation efficiency, phantom studies, and tissue studies have been conducted. The applicator includes a deployable monitoring system to measure the thermal distribution in the target regions, one on either side of the urethra. The functionality of the system has been confirmed through tests using phantom and ex-vivo tissue models.

Transurethral and Transvaginal High Intensity Concentrated Ultrasound (THICU) Applicator Probes—Acoustic applicators are designed based upon simulation studies of power deposition in 3D acoustic models using existing analysis tools. Parametric studies have been conducted for varying tissue acoustic properties, frequency of operation, and perfusion levels. Final designs are linear arrays of curvilinear transducers that are "soft focused" in the target region based upon the female pelvic anatomy. These designs are being optimized using the simulation and parametric analyses. Specific applicators for this clinical use are fabricated and tested for radiation efficiency, frequency bandwidth, power handling capability, and control of power deposition in anatomically-correct representative phantoms. The SAR and temperature distributions in these phantoms is measured and analyzed.

THICU controller, ultrasound monitoring, and software control program—Software for control of the therapy delivery using existing digitally-controlled generator designs and incorporating monitoring feedback for active on-line real-time feedback. Initially, therapy is monitored using existing fine mangunum-constantine wire thermocouple arrays which are deployed in very fine needles or along the surface of the probe. Measurements in the volumes of interest use a multi-channel monitoring system. Real-time thermal dose is computed real time from measured data. A diagnostic array of the ultrasound system (Sonix MDP, BK, or Terason 3000) is operated at pulse/receive mode and at a frequency of between 6.5-11 MHz and focused at a depth of 1 to 3 cm. An additional advantage to this setup is the fact that the spectrum of the diagnostic transducer will not be affected by the harmonics from the therapy spectrum, since the diagnostic frequency is generally lower than the therapy one.

Results in ex-vivo animal tissues and in realistic phantom models—Using the system and therapy probe applicators developed for transvaginal therapy delivery, the efficiency and control of thermal dose delivery to the fascial tissues irradiated is determined. Some implementations of present invention include an integrated high intensity concentrated ultrasound probe to elevate the temperature of a relative narrow thickness tissue region with minimal elevation to the tissue immediately proximal (along vaginal lining) and distal (beyond target boundary) of that region.

THICU Applicator Probes

Fabrication of the applicators follow techniques using tubular sections and angular sectored piezoceramic ultrasound transducers (operating frequency 6-9 MHz) and active water-cooling of the transducer crystals. Development of these applicators focuses on several key design considerations in order to provide sufficient power output (20-30 W/cm$^2$ applied power) with controlled heating: transducer selection, catheter materials, effective cooling, acoustic control/directionality, and robustness/durability. Benchmark testing is used for acoustic characterization and initial feedback of applicator performance during the development process. Several design iterations have been performed and bench tested in phantoms and tissues.

Figure 11:
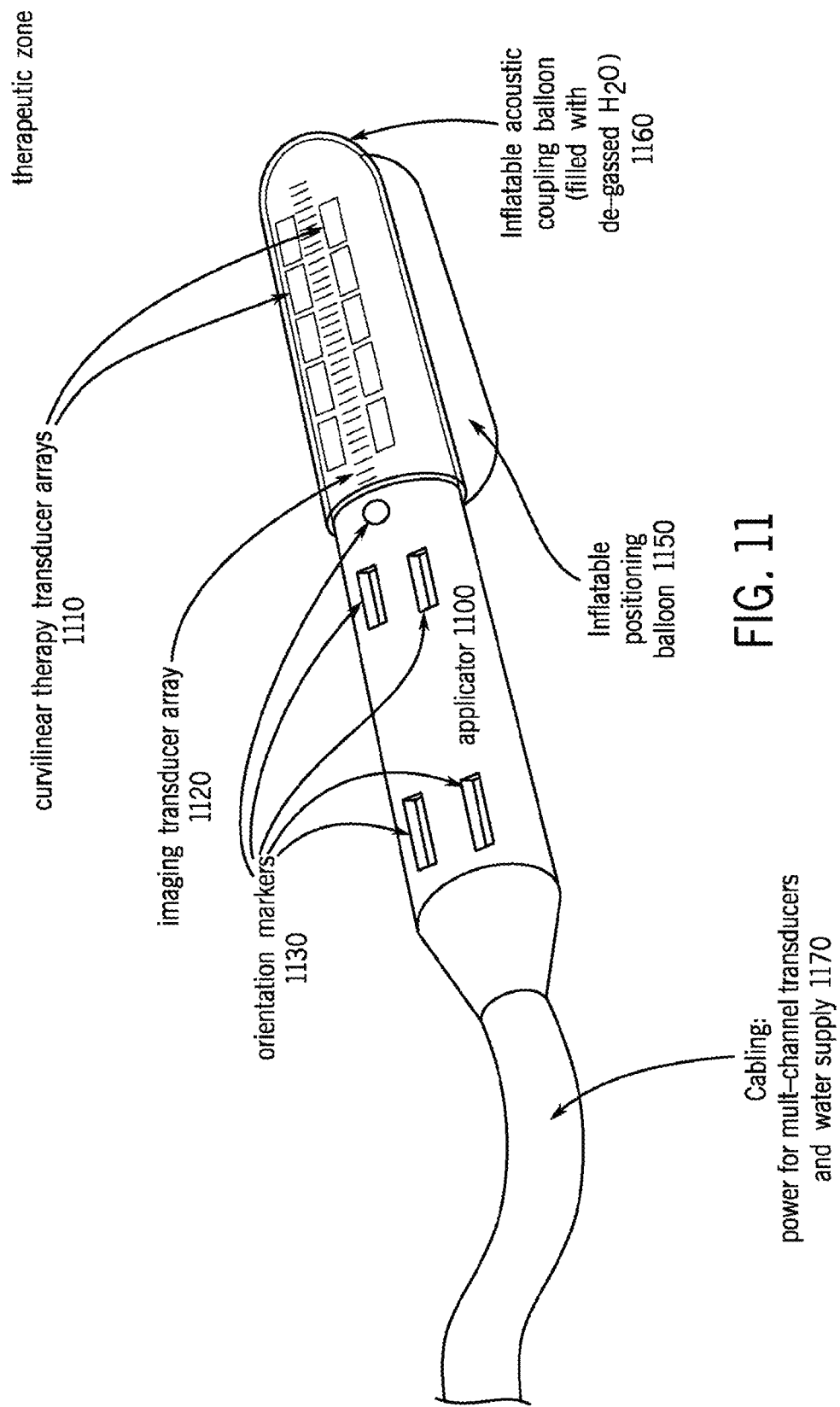
FIG. 11 illustrates a view of transvaginal applicator design concept drawing. Applicator contains two curvilinear arrays of high efficiency curved therapy transducers at locations that will direct energy beyond the vaginal mucosa and submucosa on either side of the urethra. Located centrally between the therapy transducer arrays is a linear phased array imaging transducer that can be swept in angular rotation using a tiny motorized drive to image both therapeutic zones and the central urethral zone.

FIG. 11 illustrates a view of an implementation of a view of transvaginal applicator 1100. Applicator 1100 contains two curvilinear arrays 1100 of high efficiency curved therapy transducers 1110 at locations that will direct energy beyond the vaginal mucosa and submucosa on either side of the urethra. Offset from the therapy transducer arrays 1110 is a linear phased array imaging transducer 1120 that can be swept in angular rotation using a tiny motorized drive to image both therapeutic zones and the central urethral zone. Orientation markers 1130 may also be provided to help orient the applicator during therapy. An inflatable positioning balloon 1150 is provided in one implementation. The positioning balloon 1150 may aid in positioning the applicator 1100 for the desired therapy. Further, an inflatable acoustic coupling balloon 1160 may be utilized in certain implementations. The acoustic coupling balloon 1160 provides for a uniform material through which the acoustic energy passes and may be utilized to displace air or bodily fluids within the treatment area. Finally, the applicator 1100 may utilize one or more cables/tubes for providing power, water, air, etc to the components described above.

Figure 12:
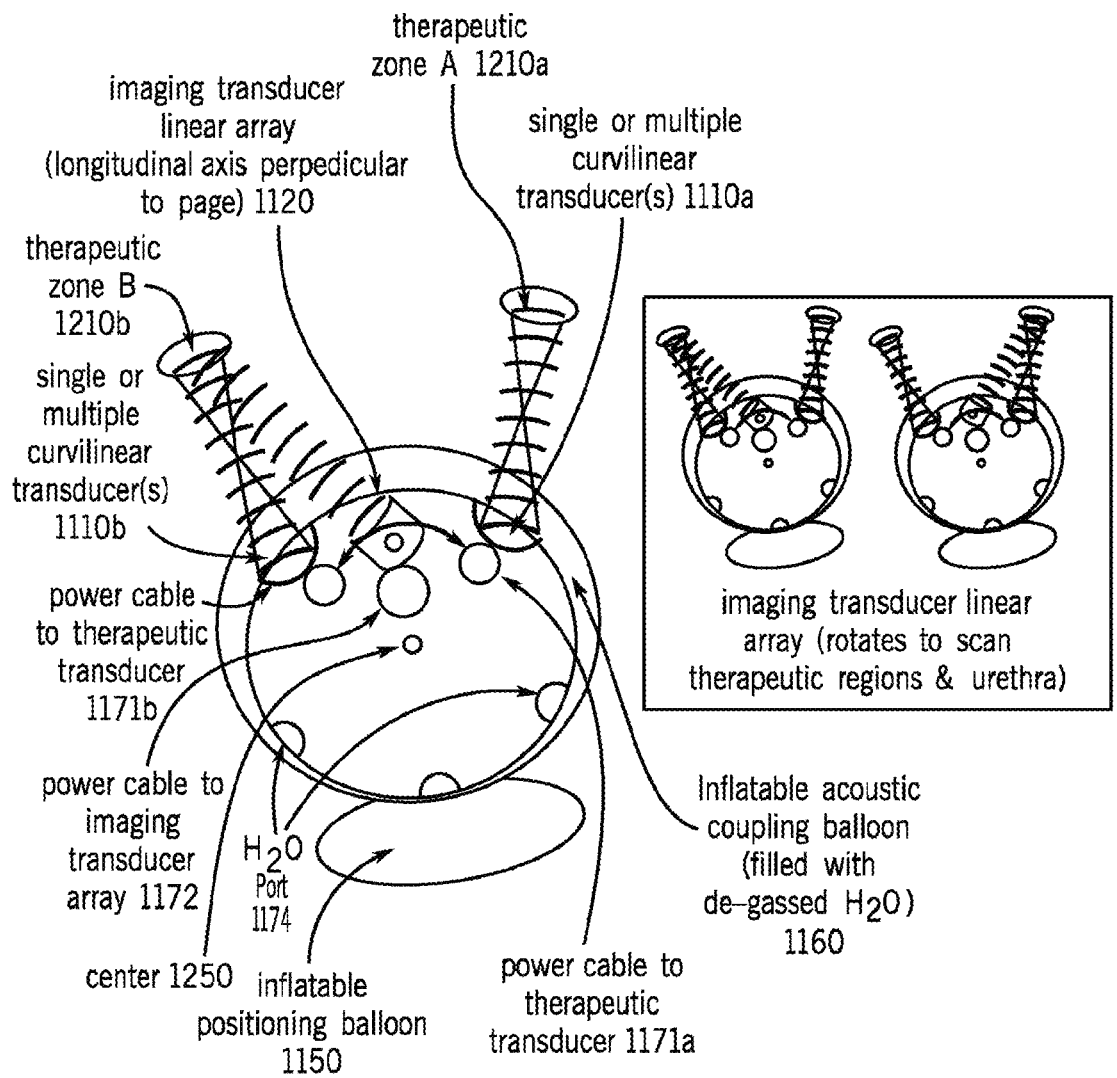
FIG. 12 illustrates a view of an implementation of a transvaginal applicator design cross-section. Applicator contains two curvilinear arrays of high efficiency curved therapy transducers at locations that will direct energy beyond the vaginal mucosa and submucosa and into endopelvic fascia or other connective urethral supporting tissues on either side of the urethra. Offset from the therapy transducer arrays is a linear phased array imaging transducer that can be swept in angular rotation using a tiny motorized drive to image both therapeutic zones and the central urethral zone. The imaging array will be used to confirm positioning and for monitoring. Ultrasound coupling and inflatable positioning balloons are shown.

FIG. 12 illustrates a view of an implementation of the transvaginal applicator 1100 in cross-section. The applicator 1100 contains two curvilinear arrays 1110*a*, 1110*b* of high efficiency curved therapy transducers at locations that will direct energy beyond the vaginal mucosa and submucosa on either side of the urethra (therapeutic zone A 1210*a* and therapeutic zone B 1210*b*). Offset from the therapy transducer arrays 1110 is a linear phased array imaging transducer 1120 that can be swept in angular rotation using a tiny motorized drive to image both therapeutic zones and the central urethral zone (illustrate in the inset image). The imaging array 1120 will be used to confirm positioning and for monitoring. Ultrasound coupling 1160 and inflatable positioning balloons 1150 are shown. Also illustrated are components of the cabling 1170: power cable 1171*a*, 1171*b* to therapeutic transducers 1110*a*, 1110*b* (respectively), power cable to the imaging transducer array 1172, and the water port 1174.

Transducers: In some implementations the applicators for high power output utilize several design parameters of both curvilinear and tubular ultrasound transducers are used, including the type of piezoceramic material, size of the transducer crystal, power handling capability, uniformity of wall thickness, efficiency optimization, electrical impedance, frequency, piezoelectric activity, electro-acoustic conversion efficiency, consistent power output, and robust coverings. Piezoceramic material selection is based on maximum power handling and crystal displacement characteristics, using comparisons between PZT-4 and PZT-8. Transducer diameter is determined by delivery site—either transvaginally or transurethrally. For transurethral, the size restriction of the external catheter, using transducers of 3.0-3.5 mm OD to maximize power output for the larger catheters. Transducers have been tested with lengths ranging from 6-15 mm, to determine an appropriate balance between axial power potential and electrical impedance. Base power-handling capability and efficiency of the transducers during protracted power delivery was tested using a force-balance technique (described below) to provide the maximum level of acoustic power output. Resulting acoustic beam output quality is characterized using the measurement technique described below. The optimal resonant frequency, electrical impedance, and piezoelectric activity of the transducers are evaluated using a network analyzer.

Catheter/Coupling Material and Cooling Schemes: Previous work with 2.4 mm OD catheter-cooled ultrasound applicators has utilized Celcon (acetal copolymer) for the catheter material. While this material has been sufficient for low to moderate power applications, it is limited at higher powers due to acoustic properties that partially block energy transmission. Selection of an improved material is based on direct comparison of thermoplastic candidates such as polycarbonate, polyether (Pebax® and Hytrel®), nylon 6-6, polyethylene, and polypropylene. Criteria used to evaluate the materials includes both acoustic properties (attenuation and impedance) and thermal properties (conductivity, melting temperature, and deflection temperature), as well as overall stiffness/durability and extrudability of the material. Selection will ultimately be based on the optimal combination of these material properties to maximize power output. Diameter and thickness of the material is selected for the appropriate applicator dimensions to provide a robust delivery device while minimizing blockage of energy transmission. The quality and quantity of acoustic energy transmission through the catheter is evaluated using measurement techniques described below. Investigations are made into cooling strategies, mechanisms, and flow schemes to achieve levels of convective cooling necessary to permit sufficient levels of applied power (30-50 W/cm$^2$ applied power). The convective heat transfer coefficient (h) inside the catheter is determined using an experimental technique in a thermal phantom developed during preliminary studies. The cooling potential of various flows are compared, as well as the cooling effects at positions along the length of the catheter. Results are also used in the theoretical simulations.

Directionality: Prior research with transurethral ultrasound applicators has demonstrated controlled and directed heating of tissue using custom transducer shapes. The proposed development work expands upon existing results, determining the ability to maintain control and directionality of tissue heating at higher power levels. Specifically, investigations are made into longitudinal control (heating control along the length of the applicator) and angular control (heating around the applicator). Multiple transducer elements (1-4) is used to achieve heating lengths of 4 cm or greater, as well as to control the length of heating with individual power to each transducer element with collimated acoustic output. Applicators are fabricated using transducers sectored to provide a specific angular acoustic region (i.e. 90° to 160°) for placement to treat the endopelvic fascia on one side while preserving critical tissue on the other side. Characterizations of both longitudinal and angular control are performed using benchtop acoustic measurements described below, and confirmed during the thermal studies.

Durability: The ultrasound applicator is integrated into the therapy probe and evaluated for general durability and robustness. These durability studies will determine thermal thresholds and mechanical thresholds for both transducers and delivery devices. Thermal testing will use direct measurements from thermocouples placed on the surface to determine operating temperatures at high power levels as well as failure limits.

Acoustic Performance Characterizations: Each of the applicators developed is characterized using experimental benchmark testing methods to determine maximum transducer power output, electro-acoustic efficiency, and acoustic beam intensity distributions as indicators of potential thermal capability. Results from these tests are used as feedback for the applicator development to ascertain levels of success and requirements for future development and testing. Power is applied to transducers using a custom generator system (0-50 W/channel, frequency range 6-10 MHz).

Acoustic Beam Distributions: The quality and pattern of the ultrasound energy output is assessed with acoustic beam distributions. Rotational beam plots (output at 360° around the applicator) is measured by 3-D scanning of a calibrated hydrophone system. This distribution of energy output is proportional to the power deposition within tissue, and is a significant characterization to determine thermal therapy potential. Axial, radial, and circumferential fields are evaluated using iso-intensity contours, and used to discern the energy patterns for fabrication techniques, material selections, and acoustic directionality.

Acoustic Power/Efficiency: Efficiency and maximum sustainable acoustic output power are important parameters to characterize performance of these applicators. The total acoustic power output and conversion efficiency is measured using force-balance techniques modified for curvilinear/cylindrical radiation sources. The acoustic efficiency as a function of frequency is determined for each applicator using static force-balance measurements. High power output characteristics are then be measured at the frequency of maximum efficiency. In order to properly assess these changes, a transient force-balance test fixture is developed that will allow measurement of acoustic output power continuously over time. A top-loading balance which holds a large cooled acoustic absorber placed within a container of water, and a jig has been fabricated which suspends the test applicator (within a 45° conical reflector) immediately over the absorbing target. This top-loading scheme removes errors associated with buoyancy changes due to target heating (versus the standard suspended target), allowing continuous measurements over a long duration to determine potential power degradation. These acoustic characteristics are used for device acceptance testing and evaluation of design parameters. A criteria used for acceptable design is minimum power application of 20-30 W/cm$^2$ with at least 40% conversion efficiency, and target of 60%.

Simulation results for different design and treatment parameters include different device configurations, operating frequencies, target distances from acoustic applicator, and treatment target temperatures. These results are shown in the graphs FIGS. 15A-C, 16A-C, with FIGS. 17A-B and 18A-B providing further information regarding variable aspects of the treatment parameters.

THICU Controller, Ultrasound Monitoring, and Software Control Program

Figure 9:
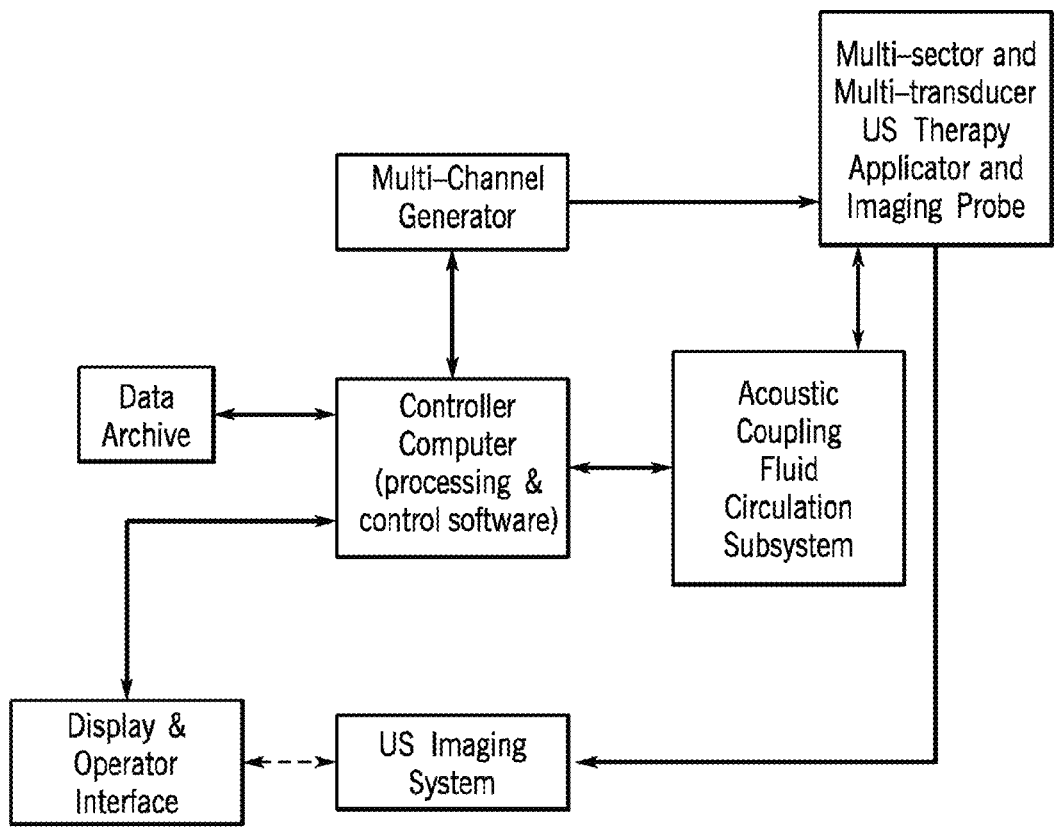
FIG. 9 illustrates one embodiment of system block diagram.

The therapy delivery system is developed including a software interface using C++ and Microsoft GDI+ and MFC to control the existing RF amplifiers (four or sixteen channel) and a 32 channel temperature measurement system. Software functionality includes user input control of RF power and frequency control for each channel, recording forward/reflected power levels, data logging amplifier parameters, and alarms at pre-set reflected power thresholds. Thermometry software includes multi-sensor temperature sensing, computing cumulative thermal dose and dose distribution, data logging, and position-labeled color bars to indicate status of each temperature point (i.e., subtherapeutic, therapeutic, max threshold). Our team has considerable experience writing both embedded and C++ software for amplifier control and temperature/dose monitoring and feedback. This system is integrated and used to control/record the thermal experiments in phantoms and excised pig tissue (Aim 3), and modified to improve & streamline operation. FIG. 9 illustrates one implementation of a system for THICU.

Materials utilized in one implementation:
Prototype THICU probe incorporating therapeutic and diagnostic imaging transducers
Prototype THICU control system and computer including therapeutic control and data acquisition for monitoring
Acoustic tissue equivalent phantom model of vagina, urethra and pelvic fascia imbedded within anthromorphic pelvic anatomical phantom
Linear arrays of multichannel manganum-constantan thermocouple sensors
Water bath to maintain environment of physiological temperature Method:
1. Thermocouple arrays are arranged to measure temperature distribution throughout the target region plus margins.
2. The tissue specimen is placed in a water bath to a level which allows the surface (to which the acoustic probe is applied) to be in normal physiological state. The water bath is set to 37° C.
3. Treatment and monitoring transducers placed in position.
4. The THICU probe is placed in position within anthromorphic pelvic anatomical phantom.
5. The THICU controller is engaged to apply energy to the tissue and forward/reflected power is monitored. Feedback and temperature control are performed by control algorithm based on imaging and interface temperature data.

Figure 10:
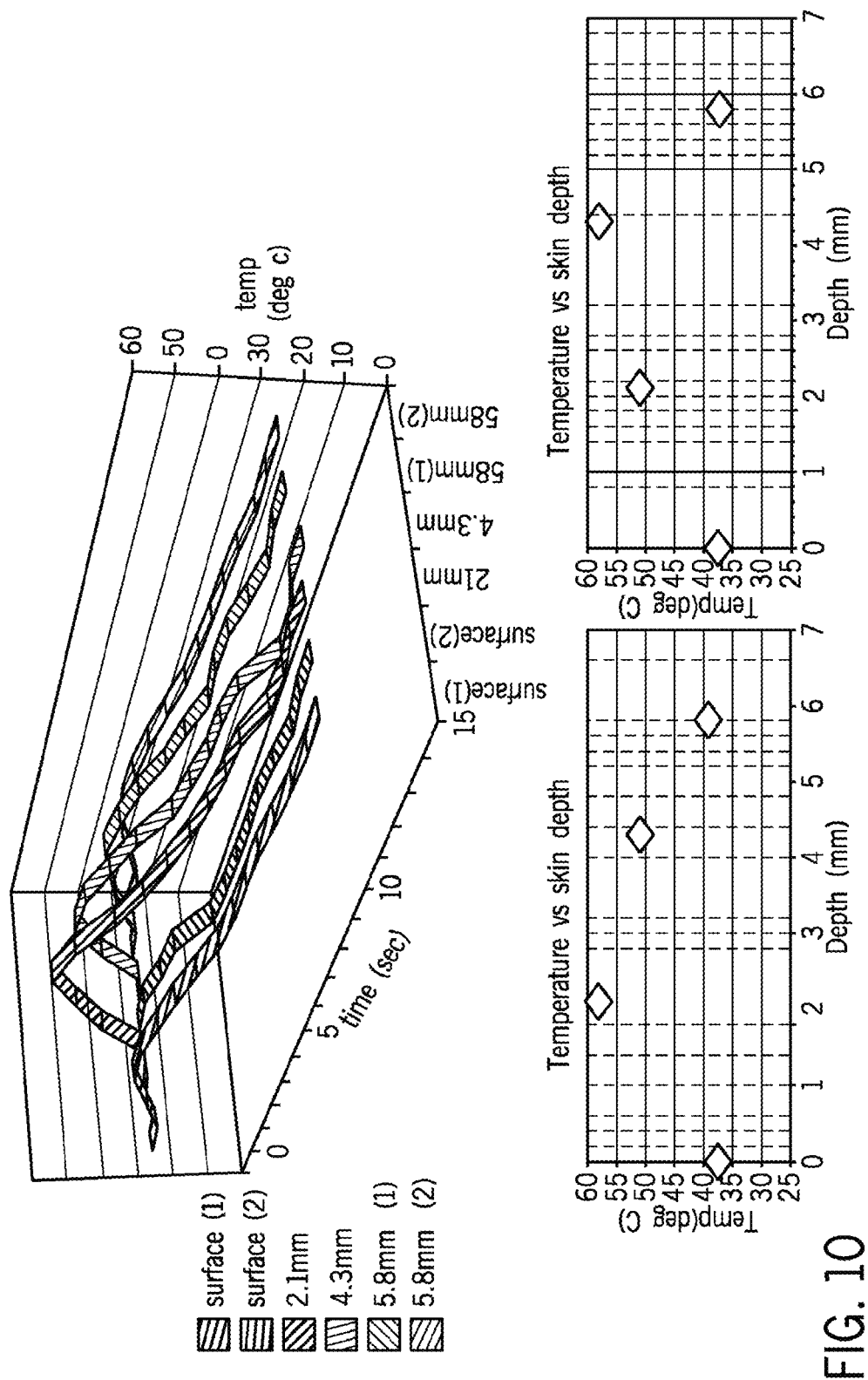
FIG. 10 illustrates results from two different curvature focused curvilinear transducers operating at 9 MHz showing control of focal depth peak and zone width.

FIG. 10 shows the results from two different focused curvilinear transducers operating at 9 MHz showing control of focal depth peak and zone$_{width}$. 1. Focal Zone—depth interval, as measured by maximum depth (measured distally from transducer) to minimal depth (measured distally from transducer) in which there is an increase in temperature greater than 45° C. if at least one of the sensors within that zone achieves a temperature of 60° C.

2. Focal Depth—the depth which has the greatest temperature of all of the levels measured and which the tissue temperature is at least 60° C.

Ultrasound imaging is used to target placement and provide image data for noninvasive monitoring of the treatment. Sensors in the coupling balloon monitor the temperature of the vaginal wall.

To test the performance of ultrasound applicators, heating trials are conducted in a phantom designed specifically for dosimetry studies to accurately mimic transvaginal and transurethral treatment conditions and in ex vivo porcine tissue, obtained immediately after euthanasia from animals used in acute experimental procedures from unrelated studies. Although there is no blood flow in the ex vivo and in vitro tissue samples, imaging studies have shown that perfusion in the fascia is typically low. These heating trials provide a controlled experimental environment where detailed and repeatable tests can be conducted for direct comparison of applicator performance (which is considerably more difficult to achieve in vivo). Thus, the use of phantoms and ex vivo tissue samples will provide the best approximation to the clinical case, and should not be viewed as a limitation of this study. The parametric evaluation of tissue perfusion effects on thermal dose is performed to identify and characterize the relevant differences in heating potential of the ultrasound applicators in vivo.

Figure 13:
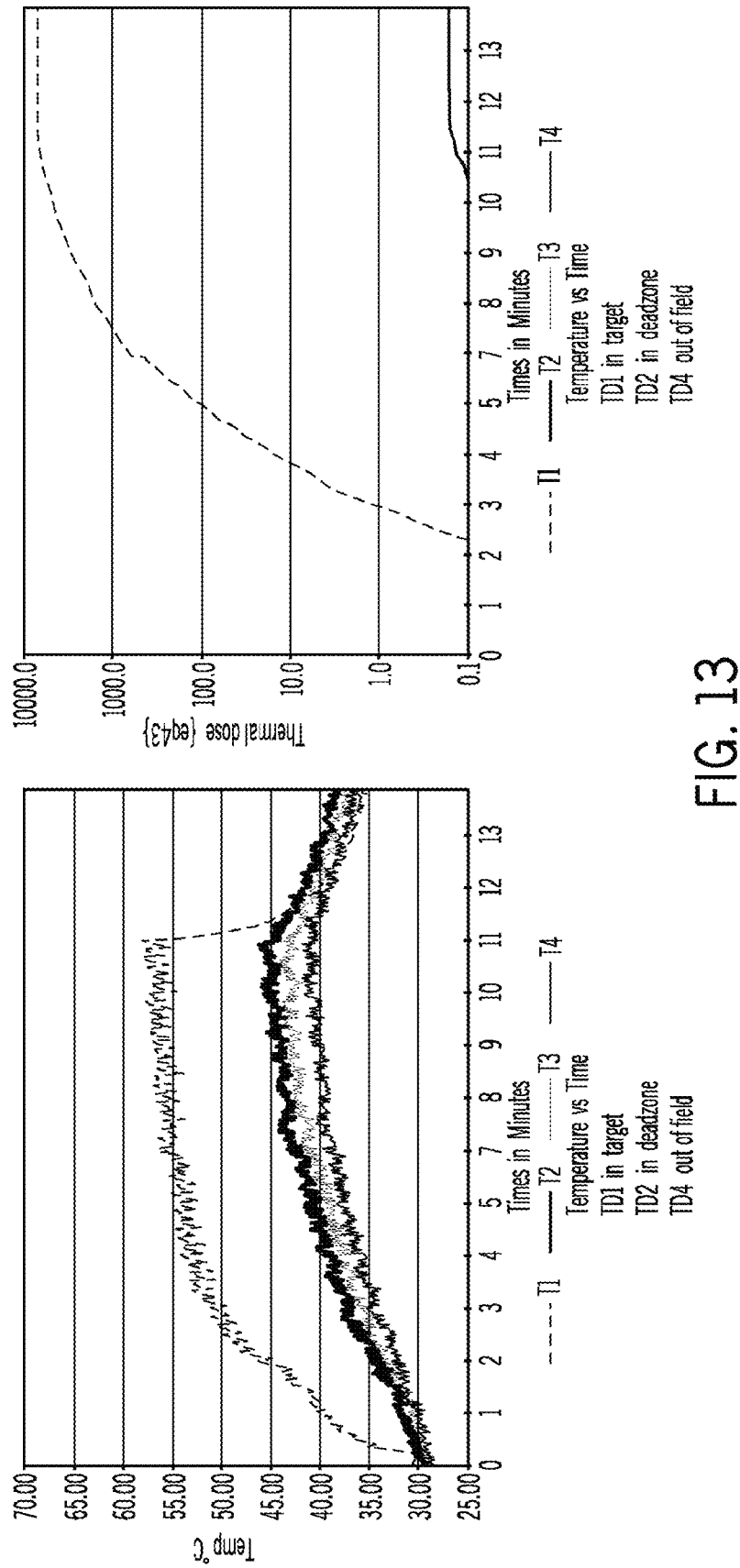
FIG. 13 illustrates dual treatment sectors and central imaging array configuration ex-vivo tissue temperature and thermal dose treatment result demonstrating treatment of tissues for a single activated therapy transducer array and in tissue located in the intended non-treated dead zone.
Figure 14A:
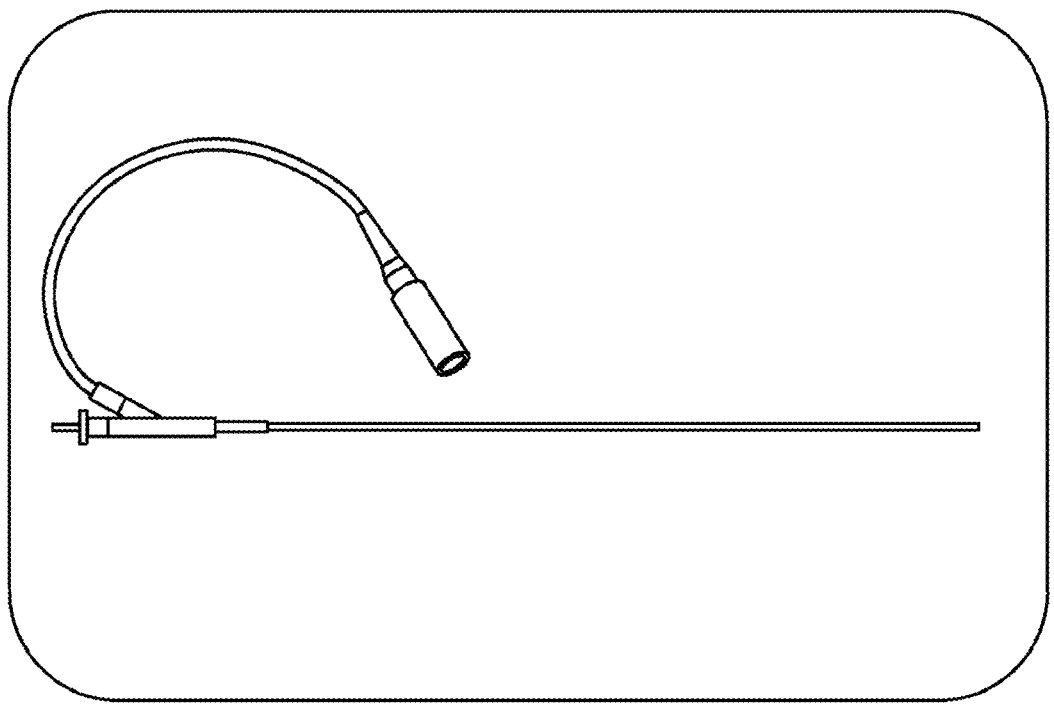
FIGS. 14A-D illustrates ultrasound delivery devices such as percutaneous ablators (14A), catheters (14B) and interstitial needles (14C) as well as a general system incorporating both ultrasound treatment generators and ultrasound imaging and 3D tracking (14D), such as an Acoustx TheraVision Ultrasound Treatment System.
Figure 14B:
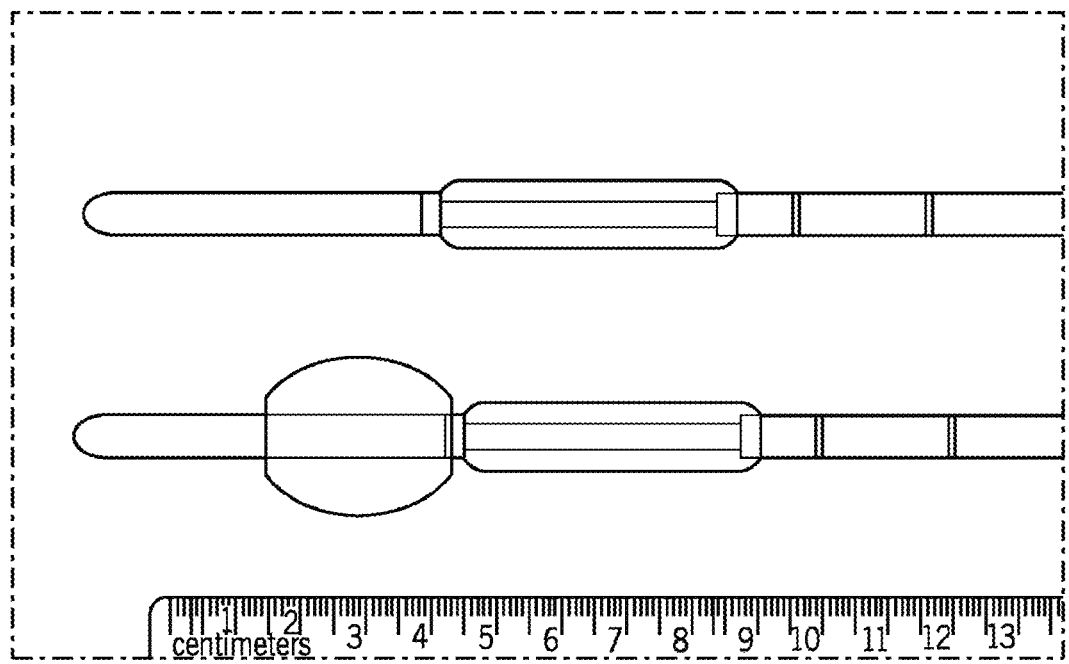
Figure 14C:
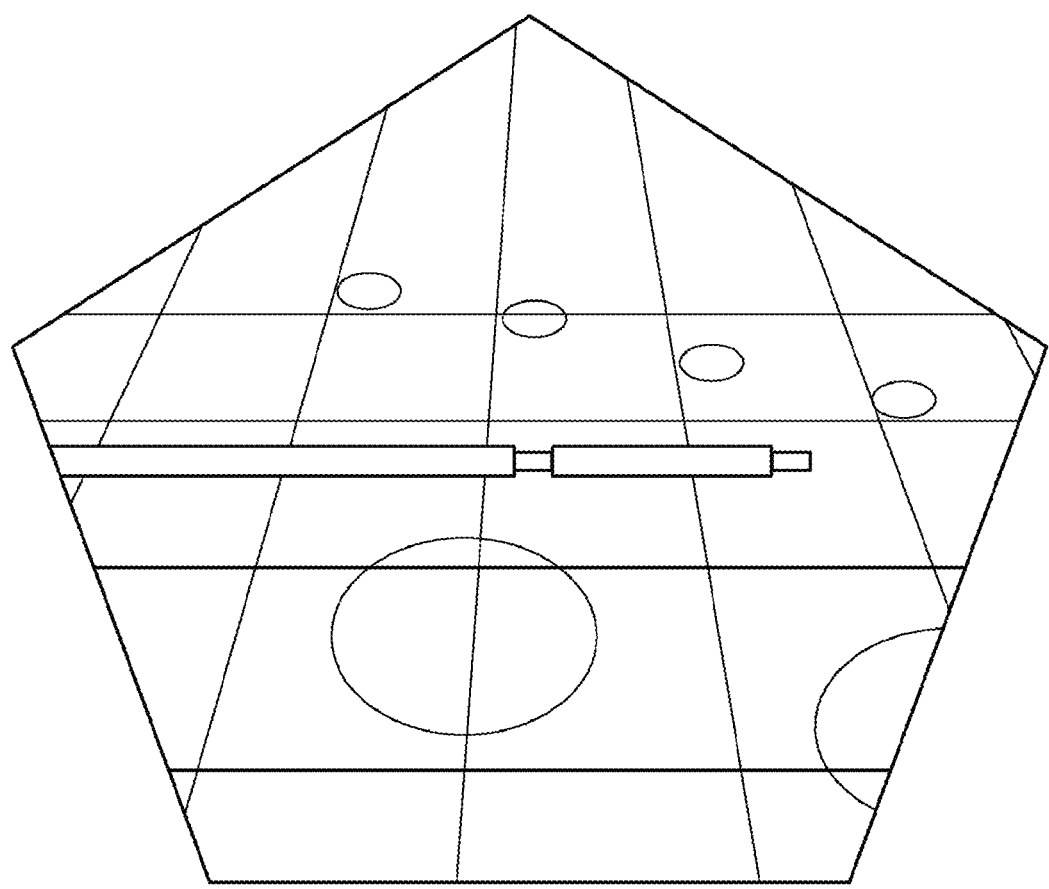
Figure 14D:
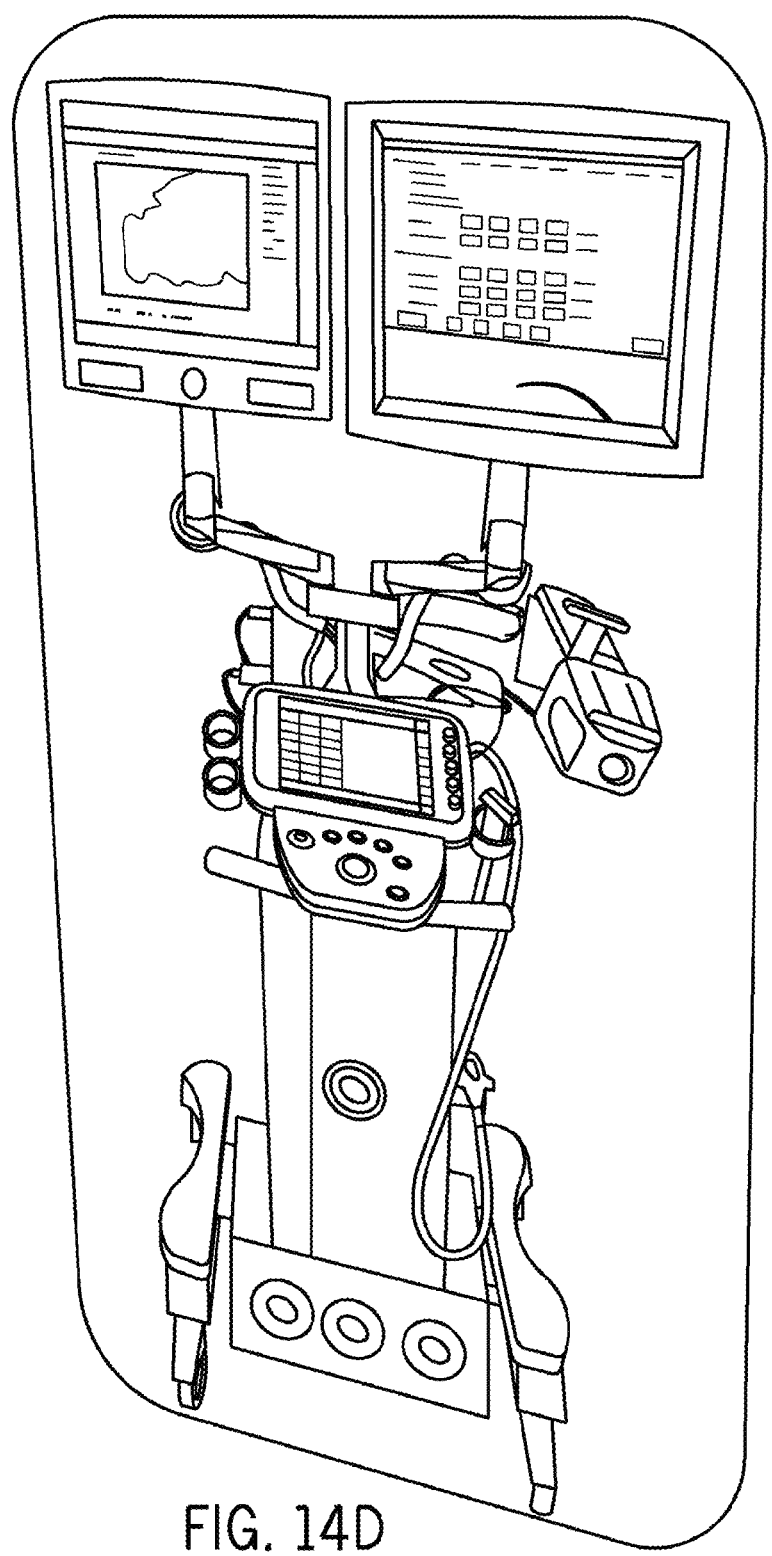
Figure 15A:
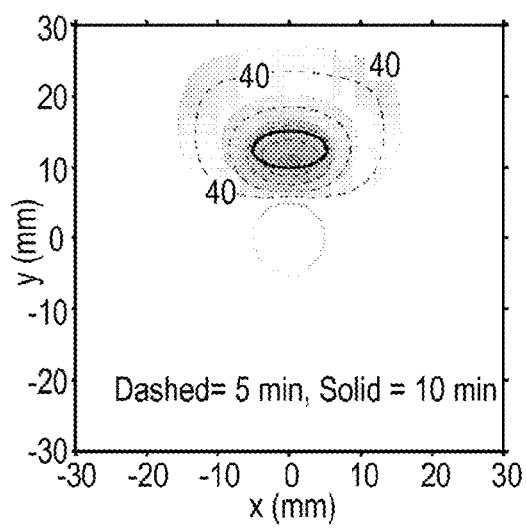
FIGS. 15A-C illustrate treatment transducer designs simulation comparisons for fascia treatment target at 5 mm from treatment applicator
Figure 15B:
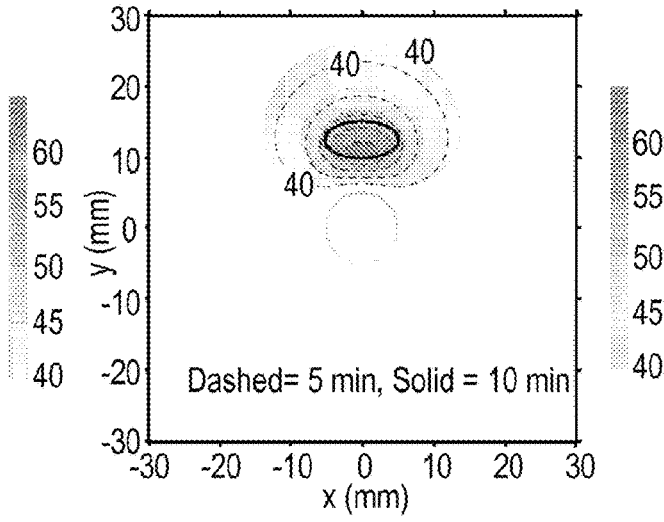
Figure 15C:
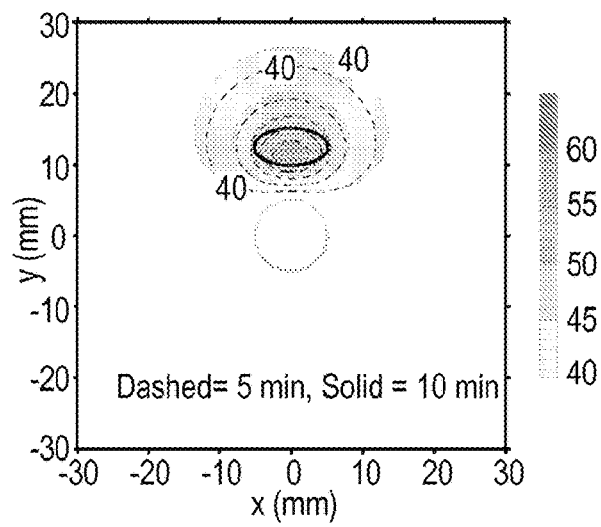
Figure 16A:
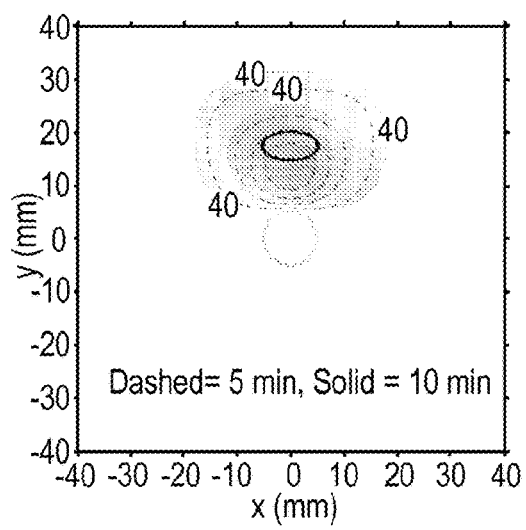
FIG. 16A-C illustrate treatment transducer designs simulation comparisons for fascia treatment target at 10 mm from treatment applicator
Figure 16B:
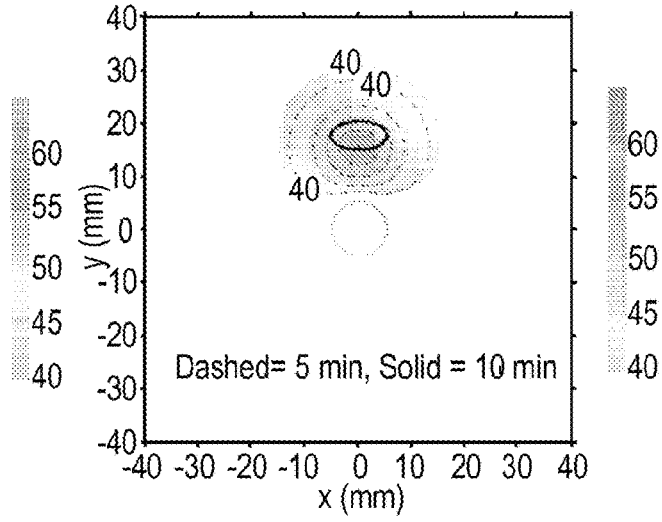
Figure 16C:
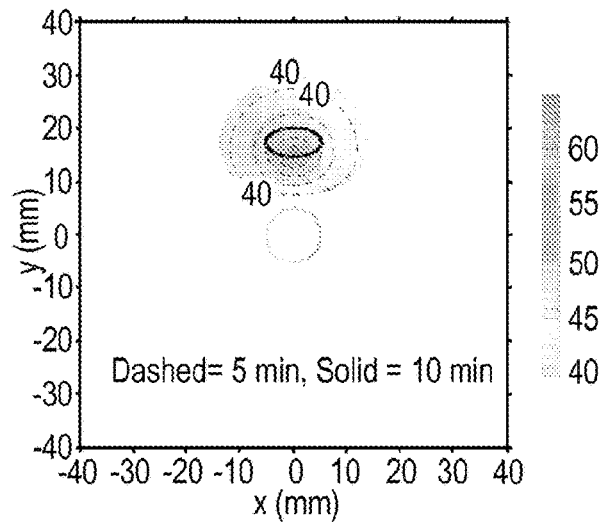
Figure 17A:
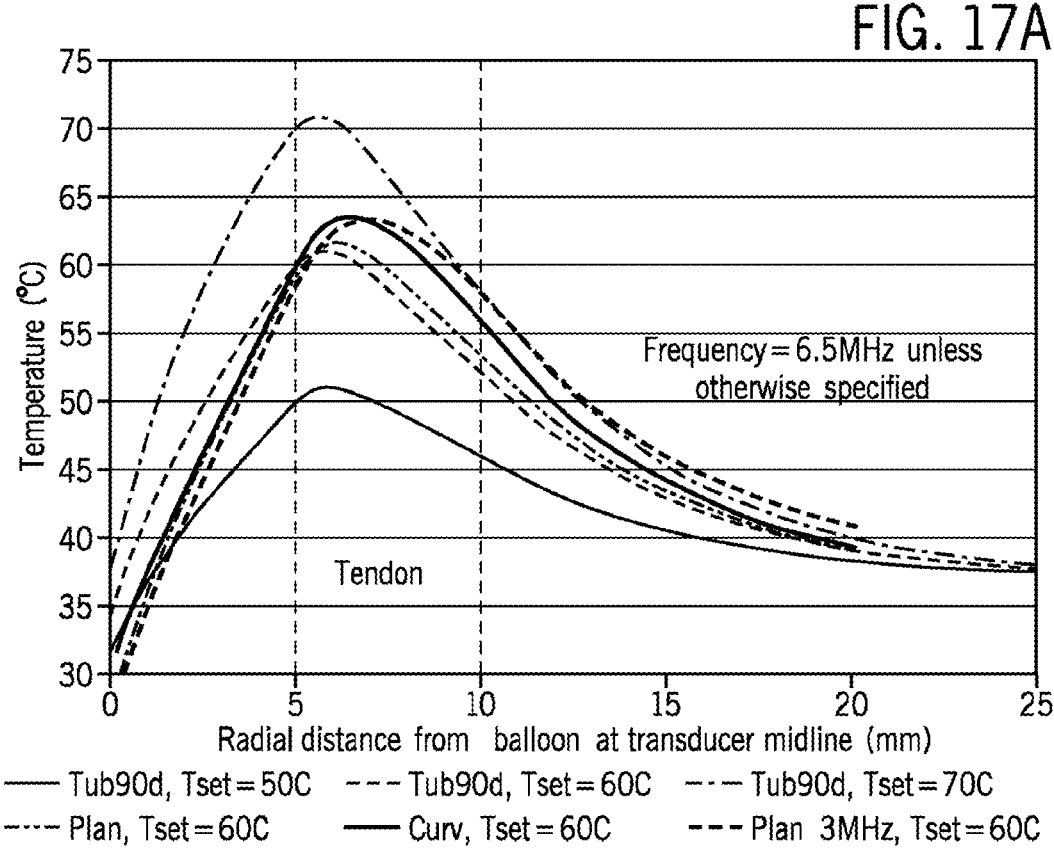
FIG. 17A-B illustrate treatment transducer designs simulation comparisons for treatment targets at 5 mm & 10 mm from treatment applicator balloon Treatment time=5 min
Figure 17B:
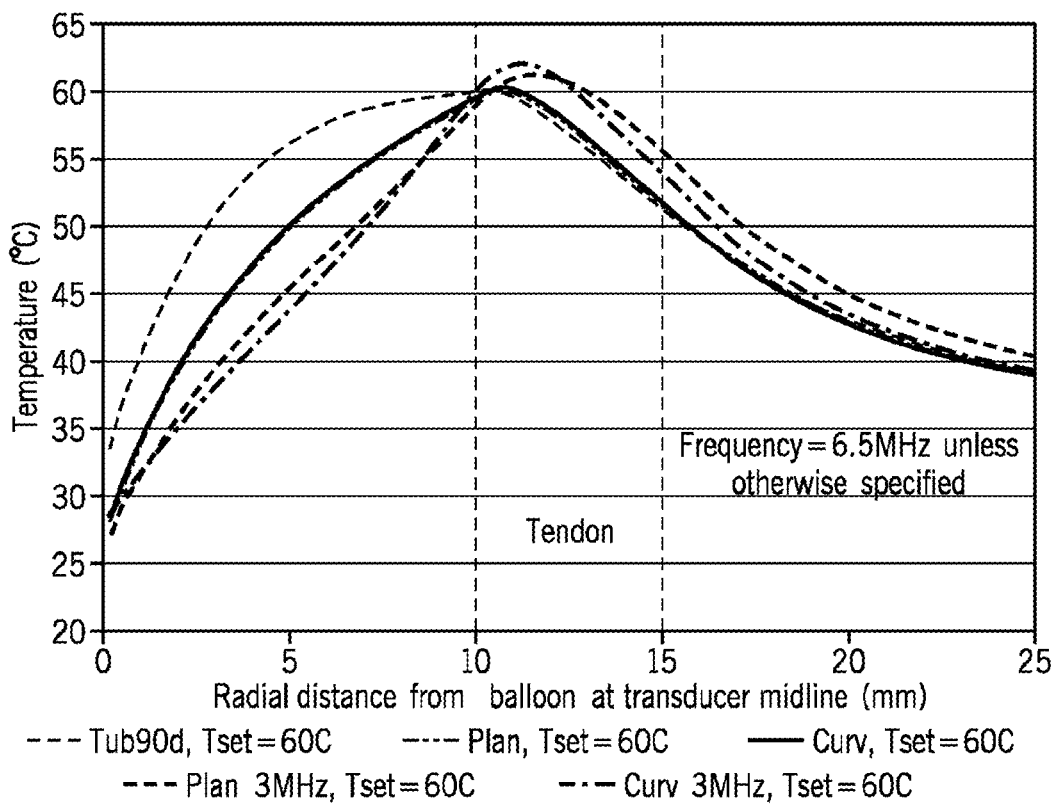
Figure 18A:
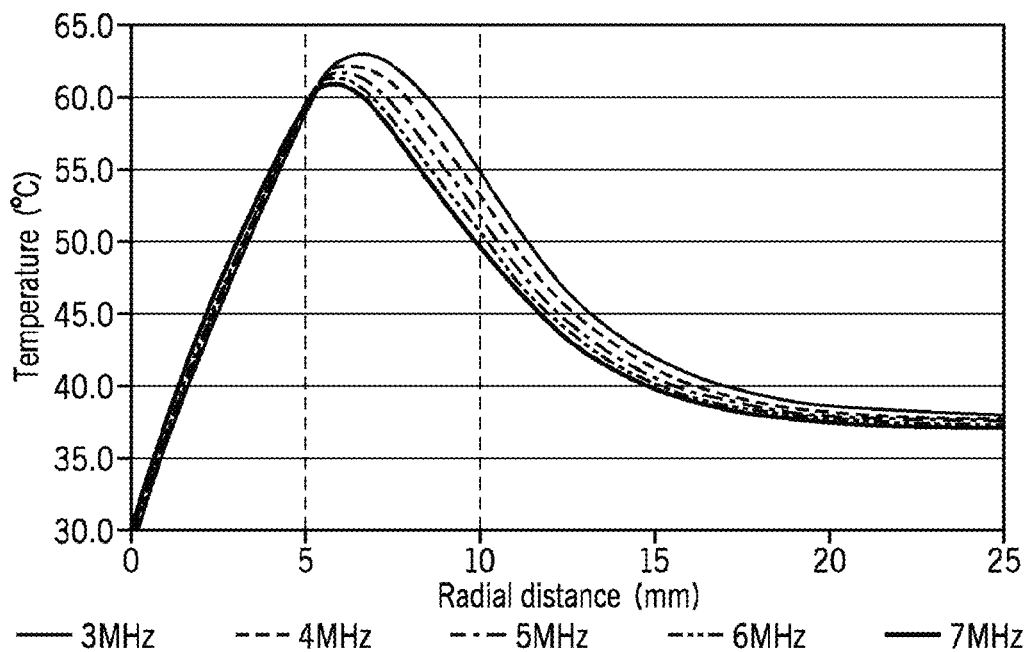
FIG. 18A-B illustrate an effect of frequency dependence on treatment depth and temperature of targeted tissue 5 mm & 10 mm from treatment applicator balloon Treatment time=2 min
Figure 18B:
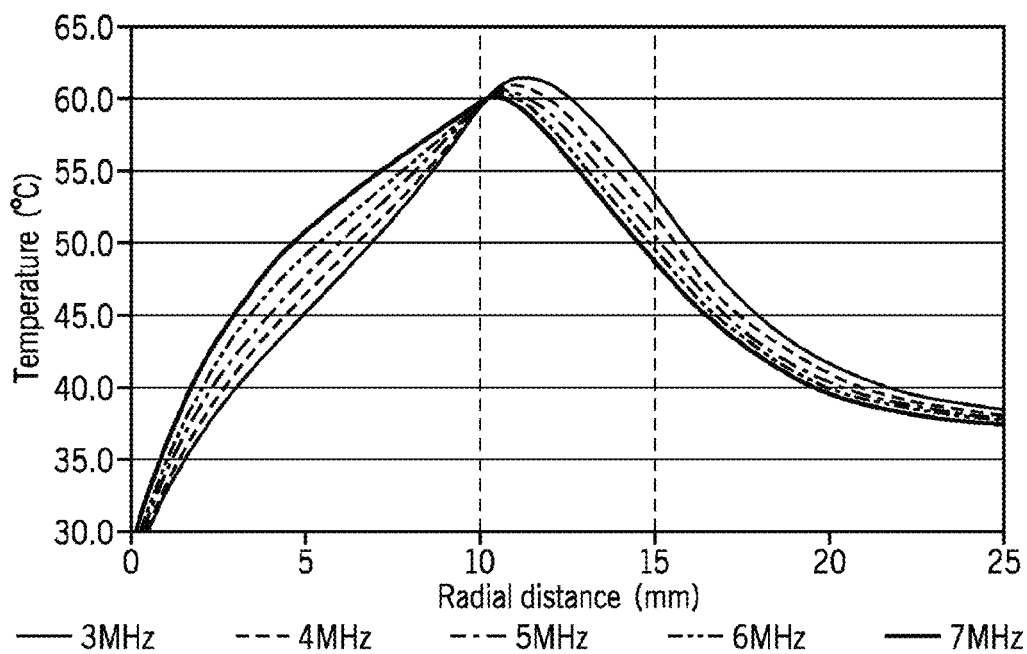
Figure 19A:
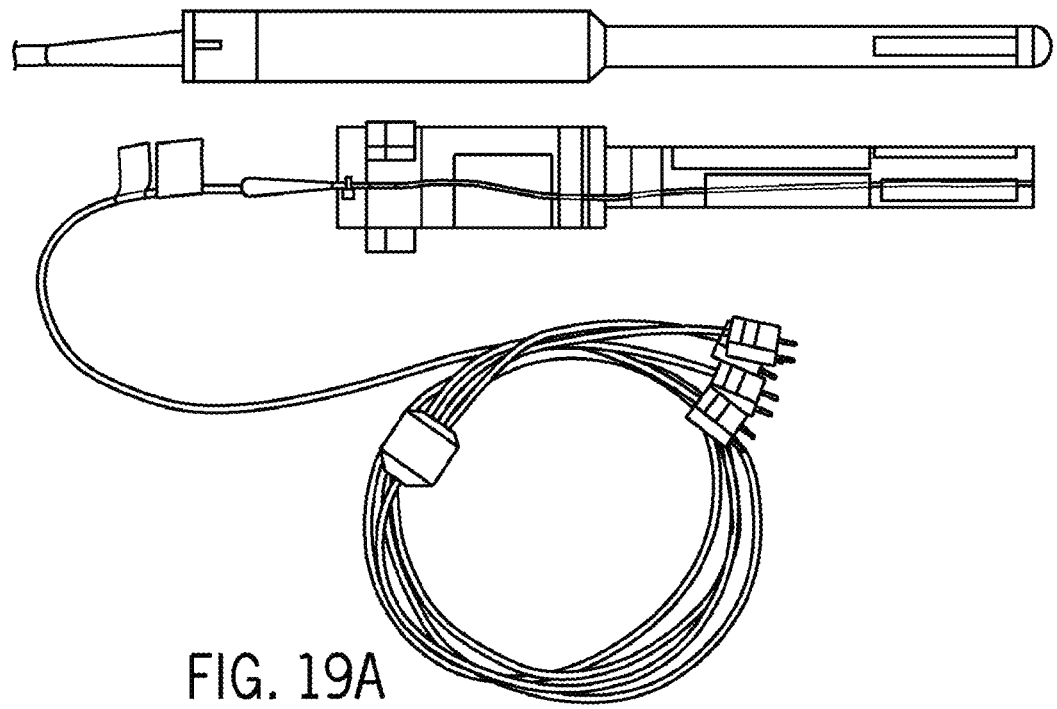
FIGS. 19A-B illustrate an implementation of Trans-Vaginal Ultrasound Thermocouple Attachment that contains 4 thermocouples on the right side of the linear aperture that are linearly spaced 5 mm apart. There are also 3 thermocouples on the left side of the aperture that are linearly spaced 1 cm apart.
Figure 19B:
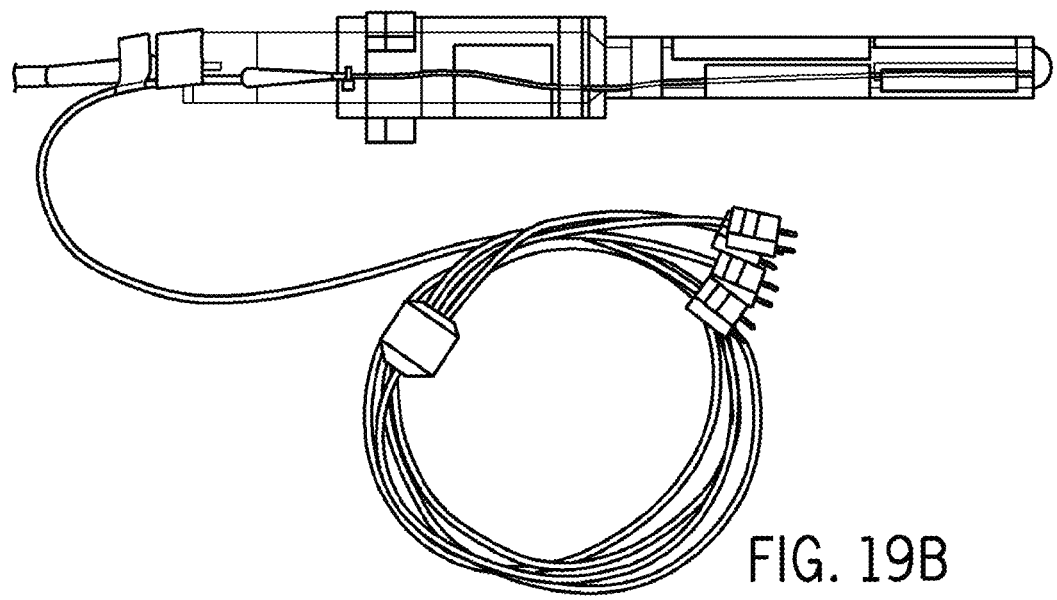
Figure 20A:
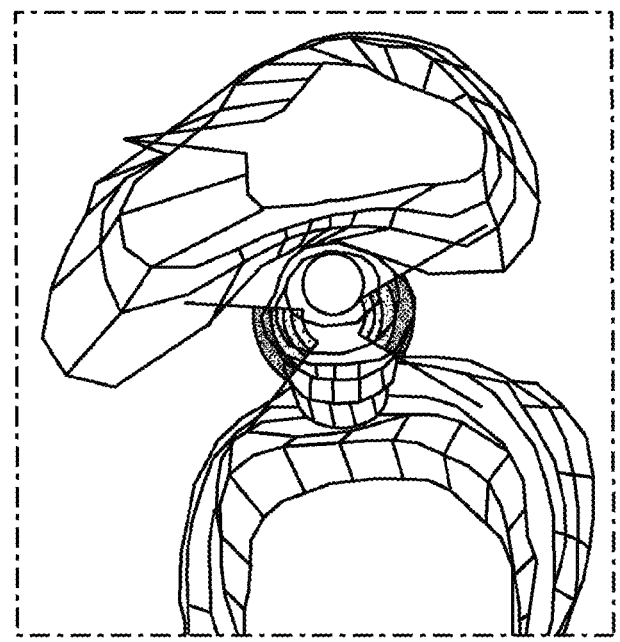
FIGS. 20A-B illustrate acoustic power deposition patterns (multi-sector directional control).
Figure 20B:
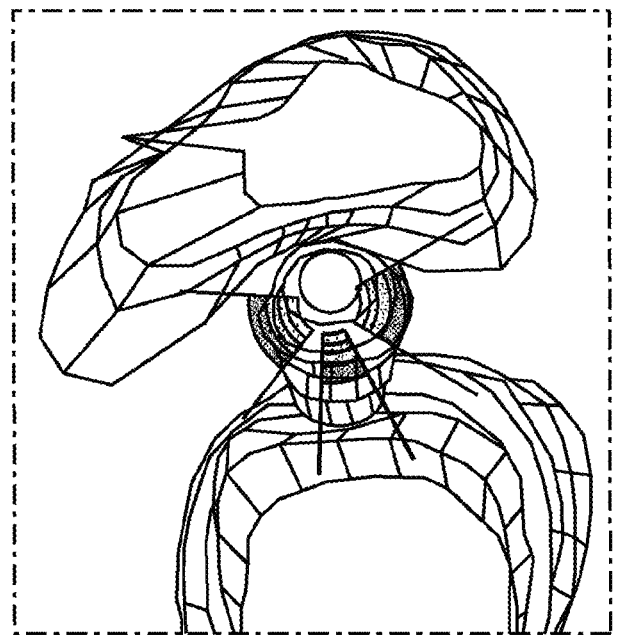
Figure 21C:
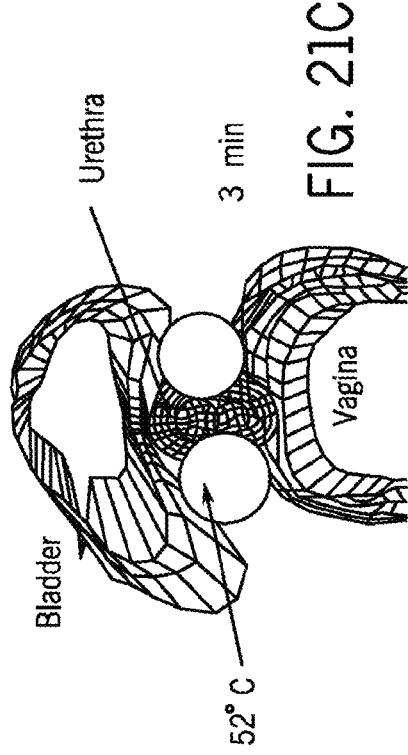
FIG. 21A-D illustrate dual sectored applicator performance (14.5 W/cm2, for 3 min and 5 min treatment durations). Dual Lateral Sectors with FIGS. 21A and 21B illustrating isotherms of 3 min and 5 min therapies respectively
Figure 21D:
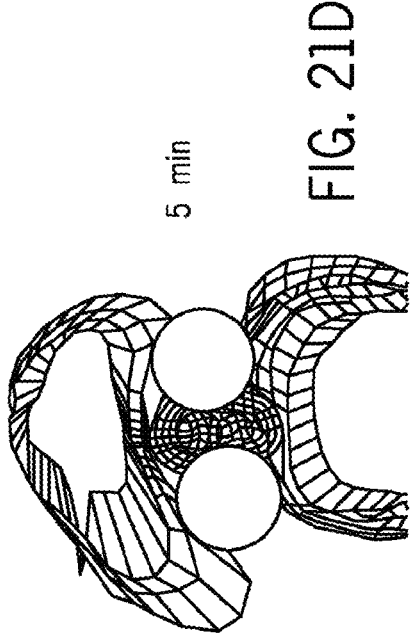
Figure 21A:
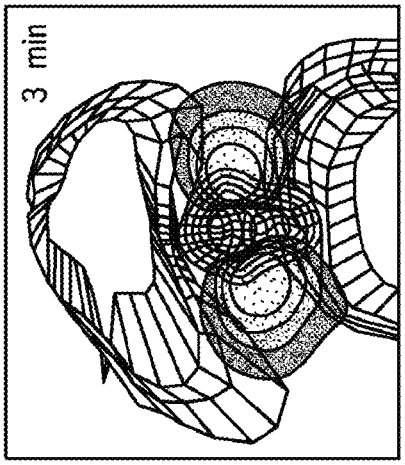
Figure 21B:
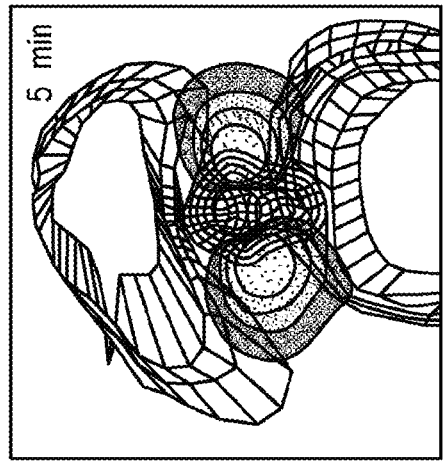
Figure 22:
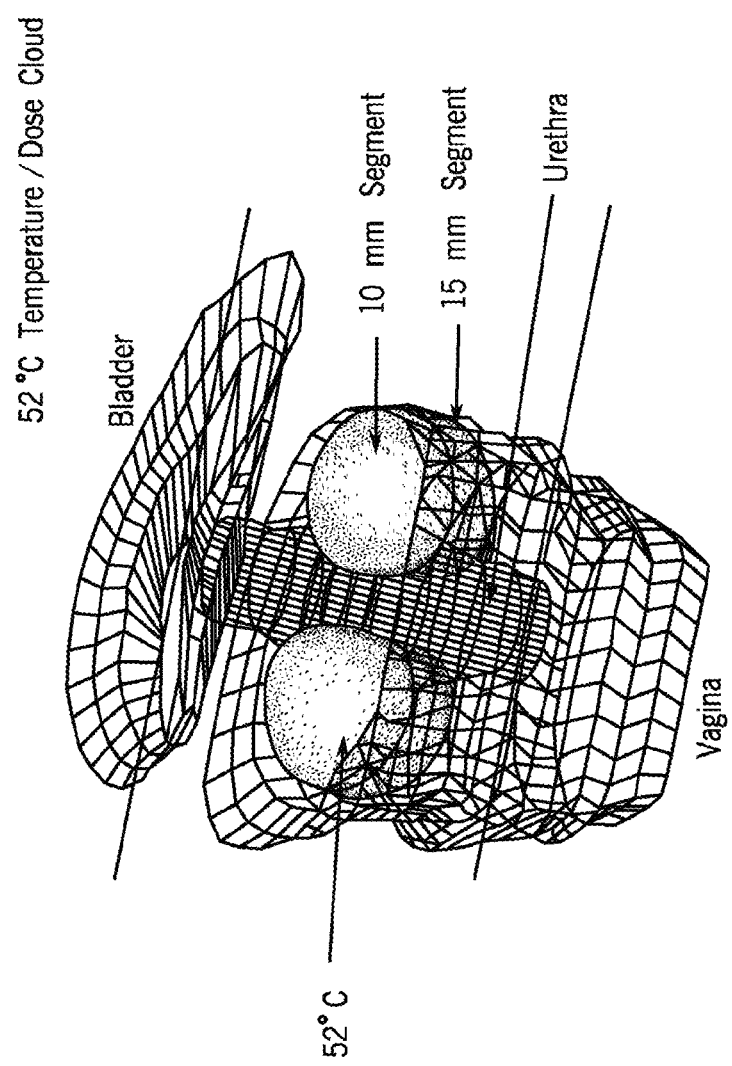
FIG. 22 illustrates an investigation of applicator Length, Dual Sectors, 10 mm vs 15 mm Transducer excited at 14.5 W/cm2.

The heating trials are performed with a therapy probe inserted into the phantom or excised tissue region, The phantom is maintained at 37° C. via a circulating water jacket built into the phantom and the ex vivo tissue is placed in a temperature-controlled water bath. Translucent and reusable polyacrylimide gel (PAG) phantoms is used to mimic the vaginal wall and surrounding soft-tissue; these PAG phantoms have thermal (k=0.56 W m-1° C.$^{-1}$) and acoustic properties (p=0.3-0.7 dB cm-1 MHz-1, c=1540 m s$^{-1}$) consistent with soft tissue. PAG phantoms have been successfully made in lab with acoustic properties representative of cervix and prostate. Striated beef muscle is degassed and used for mimicking fascia. Arrays of miniature thermocouple probes are placed in the tissue, using a template to ensure proper alignment. These probes are custom made multiple junction constantan-manganin sensors, encased in thin-walled polyimide tubing, and inserted within 22-g thin walled needles—this configuration has minimal thermal conduction and ultrasound artifact. These thermocouples is used to measure radial and axial temperature distributions (and resulting thermal dose) in the tissue during all heating experiments, and is recorded using a 32-channel thermometry system with fast data acquisition interfaced to a computer. Placement verification and targeting is performed using a diagnostic ultrasound. The diagnostic image is used to monitor acoustic changes based on the method described in the previous section. The image is processed using unique pattern recognition algorithms for noninvasive treatment monitoring as a result of tissue stiffness changes due to ablation. Another method, acoustic vibration imaging, has been shown to be feasible for monitoring externally focused ultrasound. The image results are spatially correlated with the thermal dose measured via implanted miniature thermocouple sensor arrays. Multiple heating trials are performed with varied applicator parameters of applied power levels, heating times, coolant flows, and active transducer elements. Following sonication, the tissue is sliced along the transverse and longitudinal axes, TTC stained, to measure the boundary and volume of visible thermal change. Measurements of the lesion formation is used to assess the uniformity of circumferential or directional heating, and the ability to provide controlled and directed heating from the transducer source. The prototype development and testing is considered successful if the applicators can effectively deliver thermal treatment within a targeted depth region between 3 mm to 15 mm of controlled thickness range of 5 mm to 15 mm in 2-5 minutes of heating, while controlling the thermal dose to the targeted geometric volume. Temperature and thermal dose in ex-vivo fresh tissue is shown in FIG. 13. The full extent of heating potential and controllability of both transvaginal and transurethral applicators is characterized with this approach.

Based on the theoretical analysis, a 60-80° acoustic dead zone between sectors is necessary in on implementation to limit nerve temperature <45° C. This acoustic dead zone size can be achieved by making a physical inactive zone. Given possible deviations in nerve location the inactive zone may be adjusted.

One implementation provides for pelvic floor stabilization. In such an implementation, the endopelvic fascia is treated. Lidocaine only (or a like aethesia) may be used. There is no need for vaginal incisions. It is anticipated that a 70% to 80% effective rate will be observed. The procedure allows for the potential of a office procedure rather than required hospitalization.

In another implementation, the system and methods are utilized for bladder neck stabilization. Lidocaine only (or a like anethestic) may be used. There is no need for vaginal incisions or needle implantation. It is anticipated that a 35% to 55% effective rate will be observed. The procedure allows for the potential of a office procedure rather than required hospitalization.

All publications and other references cited herein are incorporated herein by reference in their entireties.

Although the description herein contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Figure 23:
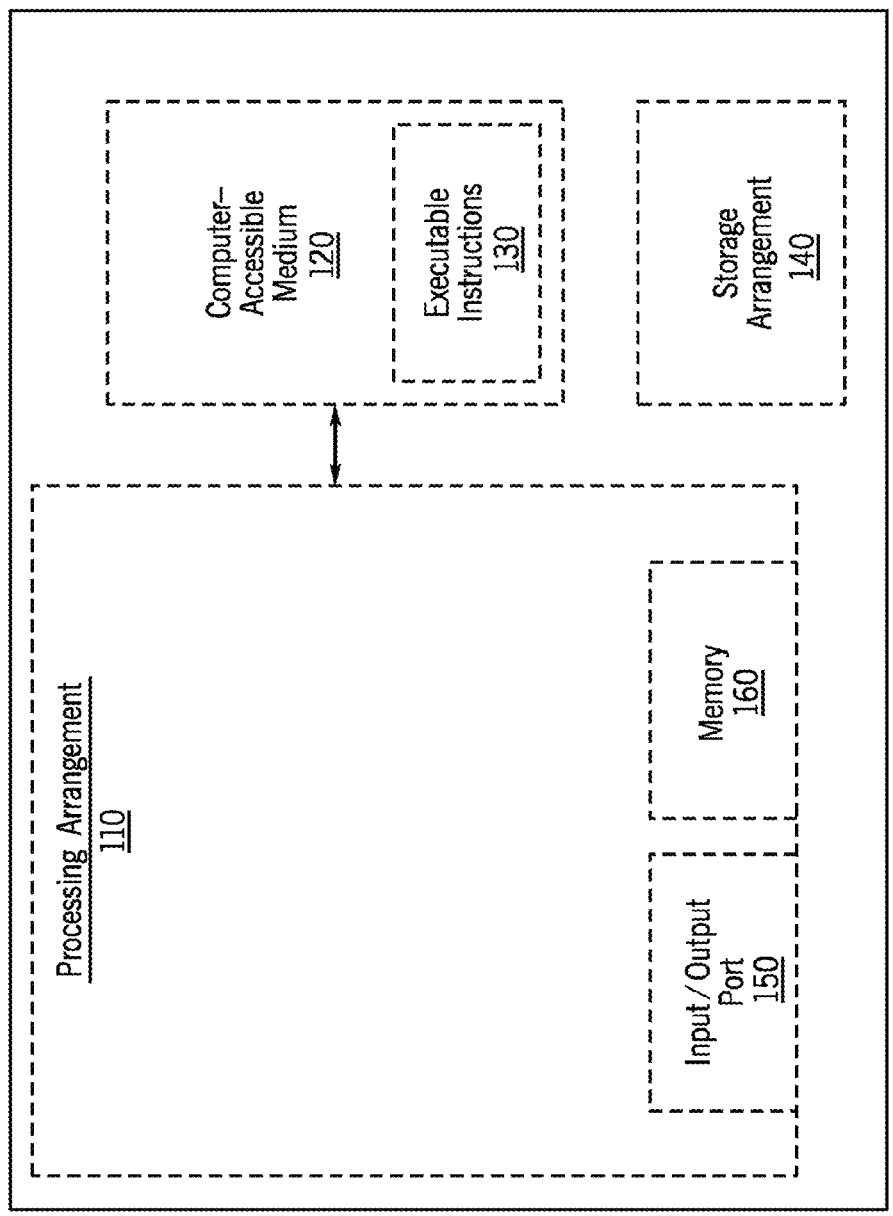
FIG. 23 illustrates an embodiment of a computer system of the present invention.

In one embodiment, shown in FIG. 23, a system 100 is provided. FIG. 23 shows an exemplary block diagram of an exemplary embodiment of a system 100 according to the present disclosure. For example, an exemplary procedure in accordance with the present disclosure can be performed by a processing arrangement 110 and/or a computing arrangement 110. Such processing/computing arrangement 110 can be, e.g., entirely or a part of, or include, but not limited to, a computer/processor that can include, e.g., one or more microprocessors, and use instructions stored on a computer-accessible medium (e.g., RAM, ROM, hard drive, or other storage device).

As shown in FIG. 4, e.g., a computer-accessible medium 120 (e.g., as described herein, a storage device such as a hard disk, floppy disk, memory stick, CD-ROM, RAM, ROM, etc., or a collection thereof) can be provided (e.g., in communication with the processing arrangement 110). The computer-accessible medium 120 may be a non-transitory computer-accessible medium. The computer-accessible medium 120 can contain executable instructions 130 thereon. In addition or alternatively, a storage arrangement 140 can be provided separately from the computer-accessible medium 120, which can provide the instructions to the processing arrangement 110 so as to configure the processing arrangement to execute certain exemplary procedures, processes and methods, as described herein, for example.

System 100 may also include a display or output device, an input device such as a key-board, mouse, touch screen or other input device, and may be connected to additional systems via a logical network. Many of the embodiments described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art can appreciate that such network computing environments can typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Various embodiments are described in the general context of method steps, which may be implemented in one embodiment by a program product including computer-executable instructions, such as program code, executed by computers in networked environments. Generally, program modules include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps.

Software and web implementations of the present invention could be accomplished with standard programming techniques with rule based logic and other logic to accomplish the various database searching steps, correlation steps, comparison steps and decision steps. It should also be noted that the words "component" and "module," as used herein and in the claims, are intended to encompass implementations using one or more lines of software code, and/or hardware implementations, and/or equipment for receiving manual inputs.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

I claim:

1. A system for treating stress urinary incontinence comprising:
 a transvaginal applicator having:
  a first planar transducer array comprising a first plurality of transducers aligned along a first array longitudinal axis, having a first therapeutic zone and a second planar transducer array, comprising a second plurality of transducers, having a second therapeutic zone, the first therapeutic zone and the second therapeutic zone are not overlapping, with a dead zone in between the first therapeutic zone and the second therapeutic zone;
  an imaging transducer array having an imaging array longitudinal axis, the imaging transducer array configured to move relative to the first planar transducer array and the second planar transducer array and pivotably positioned about the imaging array longitudinal axis relative to the first planar transducer array and the second planar transducer array, wherein the imaging transducer array is positioned to pivotally scan the first therapeutic zone, then the dead zone, and then the second therapeutic zone;
  an acoustic coupling balloon; and
  a positioning balloon.

2. The system of claim 1, further comprising orientation markers.

3. The system of claim 1, wherein the first planar transducer array and the second planar transducer array are positioned at 50 degrees to 70 degrees with respect to each other.

4. The system of claim 1, further comprising an acoustic coupling fluid circulation subsystem coupled to the acoustic coupling balloon.

5. The system of claim 1, further comprising a multi-channel generator coupled to at least one of the first planar transducer array and the second planar transducer array.

6. The system of claim 1, further comprising an ultrasound imaging system coupled to the imaging transducer array.

7. The system of claim 1, wherein the applicator is selected from the group consisting of therapeutic ultrasound device, catheter, and interstitial needle.

8. A method of treating stress urinary incontinence comprising:
 identifying an anatomic structure beyond a vaginal mucosa and submucosa on either side of a urethra to be treated by an applicator, the applicator comprising:
  a first planar transducer array;
  a second planar transducer array;
  an imaging transducer array pivotable between the first planar transducer array and the second planar transducer array;
  an acoustic coupling balloon; and
  a positioning balloon;
 mapping a treatment focal depth and a treatment focal zone;
 placing the applicator at the anatomic structure;
 inflating the positioning balloon, maintaining a position of the applicator;
 inflating the acoustic coupling balloon;
 applying acoustic energy to a first therapeutic zone associated with the first planar transducer array and to a second therapeutic zone associated with the second planar transducer array, wherein the first therapeutic zone and the second therapeutic zone are not overlapping, with a central urethral dead zone in between the first therapeutic zone and the second therapeutic zone, to raise a temperature of at least a portion of the anatomic structure to 50° C. to 80° C. for a period of time in a range between at least 2 minutes and 5 minutes, the period of time sufficient to affect remodeling of a collagenous structure of the portion of the anatomic structure; and pivoting the imaging transducer array to image the first therapeutic zone, the central urethral dead zone, and the second therapeutic zone, confirming the position of the applicator and monitoring changes in tissue density and elasticity in the portion of the anatomic structure.

9. The method of claim 8, wherein the anatomic structure comprises an endopelvic fascia.

10. The method of claim 8, wherein the anatomic structure comprises a bladder neck.

11. The method of claim 8, wherein the first therapeutic zone and the second therapeutic zone include a region there between wherein the temperature remains below 50° C.

12. A computer-implemented system for treatment of stress urinary incontinence, comprising:
   a processor; and
   a tangible computer-readable medium operatively connected to the processor and including computer code configured to:
      identify an anatomic structure beyond a vaginal mucosa and submucosa on either side of the urethra to be treated by an applicator, the applicator comprising:
         a first planar transducer array;
         a second planar transducer array;
         an imaging transducer array configured to pivot between the first planar transducer array and the second planar transducer array;
         an acoustic coupling balloon; and
         a positioning balloon;
      map a treatment focal depth and a treatment focal zone;
      place the applicator at the anatomic structure;
      inflate the positioning balloon to maintain a position of the applicator;
      inflate the acoustic coupling balloon;
      apply acoustic energy to a first therapeutic zone associated with the first planar transducer array and to a second therapeutic zone associated with the second planar transducer array, wherein the first therapeutic zone and the second therapeutic zone are not overlapping, with a central urethral dead zone between the first therapeutic zone and the second therapeutic zone, to raise a temperature of at least a portion of the anatomic structure to 50° C. to 80° C. for a period of time in a range between at least 2 minutes and 5 minutes, the period of time sufficient to affect remodeling of a collagenous structure of the portion of the anatomic structure; and
      pivot the imaging transducer array to image the first therapeutic zone, the central urethral dead zone, and the second therapeutic zone, confirming the position of the applicator and monitoring changes in tissue density and elasticity in the portion of the anatomic structure.

13. The system of claim 12, wherein the first therapeutic zone and the second therapeutic zone include a region there between wherein the temperature remains below 50° C.

14. The system of claim 12 further comprising the applicator in communication with the computer code.

* * * * *